(12) United States Patent
Palushi et al.

(10) Patent No.: US 10,736,647 B2
(45) Date of Patent: Aug. 11, 2020

(54) DILATION CATHETER WITH NAVIGATION SENSOR AND VENT PASSAGEWAY IN TIP

(71) Applicants: Acclarent, Inc., Irvine, CA (US); Biosense Webster (Israel) Ltd., Yokneam (IL)

(72) Inventors: Jetmir Palushi, Irvine, CA (US); Henry F. Salazar, Pico Rivera, CA (US); Fatemeh Akbarian, Rancho Palos Verdes, CA (US); Vadim Gliner, Haifa (IL); David A. Smith, Jr., Lake Forest, CA (US); Itzhak Fang, Irvine, CA (US)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 255 days.

(21) Appl. No.: 15/797,049

(22) Filed: Oct. 30, 2017

(65) Prior Publication Data
US 2019/0125375 A1 May 2, 2019

(51) Int. Cl.
*A61B 17/24* (2006.01)
*A61M 25/10* (2013.01)
(Continued)

(52) U.S. Cl.
CPC ............. *A61B 17/24* (2013.01); *A61B 1/00* (2013.01); *A61B 1/002* (2013.01); *A61B 1/227* (2013.01);
(Continued)

(58) Field of Classification Search
CPC . A61B 34/20; A61B 17/24; A61B 2034/2051; A61B 2090/365; A61B 1/233; A61B 2090/3983; A61B 2017/22051; A61B 2017/22061; A61B 2090/3958; A61B 5/062; A61B 1/00; A61B 1/00082;
(Continued)

(56) References Cited

U.S. PATENT DOCUMENTS 7,720,521 B2  5/2010  Chang et al.
8,123,722 B2  2/2012  Chang et al.
(Continued)

OTHER PUBLICATIONS

European Search Report for EP 18 203 120.3 dated Jun. 28, 2019 (Year: 2019).*

(Continued)

*Primary Examiner* — Katherine M Shi
(74) *Attorney, Agent, or Firm* — Frost Brown Todd LLC

(57) ABSTRACT

A dilation catheter includes a catheter shaft, an expandable element, and a navigation sensor. The catheter shaft has a proximal shaft portion defining a proximal shaft end, a distal shaft portion defining a distal shaft end, and a working lumen extending between the proximal and distal shaft ends. The expandable element is disposed on the distal shaft portion proximally of the distal shaft end, and is configured to expand to dilate an anatomical passageway of a patient. The navigation sensor is arranged at the distal shaft portion, and is configured to generate a signal corresponding to a location of the distal shaft portion within the patient. In various examples, the dilation catheter may further include a bulbous distal tip, and the navigation sensor may be arranged within the bulbous distal tip.

20 Claims, 14 Drawing Sheets

(51) Int. Cl.

| | |
|---|---|
| *A61M 29/02* | (2006.01) |
| *A61B 1/00* | (2006.01) |
| *A61B 1/002* | (2006.01) |
| *A61B 1/227* | (2006.01) |
| *A61B 17/22* | (2006.01) |
| *A61F 11/00* | (2006.01) |
| *A61M 25/01* | (2006.01) |
| *A61B 34/20* | (2016.01) |
| *A61B 90/00* | (2016.01) |
| *A61B 17/00* | (2006.01) |
| *A61M 25/06* | (2006.01) |

(52) U.S. Cl.
CPC ............ *A61B 17/22* (2013.01); *A61F 11/004* (2013.01); *A61M 25/01* (2013.01); *A61M 25/10* (2013.01); *A61M 29/02* (2013.01); *A61B 34/20* (2016.02); *A61B 2017/00787* (2013.01); *A61B 2017/22051* (2013.01); *A61B 2017/22069* (2013.01); *A61B 2034/2051* (2016.02); *A61B 2090/3966* (2016.02); *A61F 11/002* (2013.01); *A61M 25/0662* (2013.01); *A61M 2210/0675* (2013.01)

(58) Field of Classification Search
CPC .......... A61B 1/227; A61B 2017/00787; A61B 2034/2072; A61B 2090/3966; A61M 25/10; A61M 2025/0037; A61M 2025/004; A61M 2210/0675; A61M 25/0161; A61M 2025/0166; A61M 2025/09066; A61F 11/002; A61F 11/004
See application file for complete search history.

(56) References Cited

U.S. PATENT DOCUMENTS

| | | | |
|---|---|---|---|
| 8,190,389 | B2 | 5/2012 | Kim et al. |
| 8,320,711 | B2 | 11/2012 | Altmann et al. |
| 8,702,626 | B1 | 4/2014 | Kim et al. |
| 9,167,961 | B2 | 10/2015 | Makower et al. |
| 9,198,736 | B2 | 12/2015 | Kim et al. |
| 2004/0097804 | A1* | 5/2004 | Sobe ................. A61B 17/3207 600/424 |
| 2007/0208252 | A1 | 9/2007 | Makower |
| 2010/0030031 | A1 | 2/2010 | Goldfarb et al. |
| 2010/0274188 | A1 | 10/2010 | Chang et al. |
| 2011/0060214 | A1 | 3/2011 | Makower |
| 2013/0274715 | A1* | 10/2013 | Chan .................... A61M 25/10 604/514 |
| 2014/0200444 | A1 | 7/2014 | Kim et al. |
| 2014/0364725 | A1 | 12/2014 | Makower |
| 2015/0374963 | A1 | 12/2015 | Chan et al. |
| 2016/0008083 | A1 | 1/2016 | Kesten et al. |
| 2016/0287059 | A1* | 10/2016 | Ha ............................ A61B 1/32 |
| 2016/0287445 | A1 | 10/2016 | Wasicek et al. |
| 2016/0310042 | A1* | 10/2016 | Kesten ................. A61B 5/055 |
| 2017/0119414 | A1 | 5/2017 | Chan et al. |

OTHER PUBLICATIONS

U.S. Appl. No. 62/555,824, entitled "Apparatus to Secure Field Generating Device to Chair," filed Sep. 8, 2017.

* cited by examiner

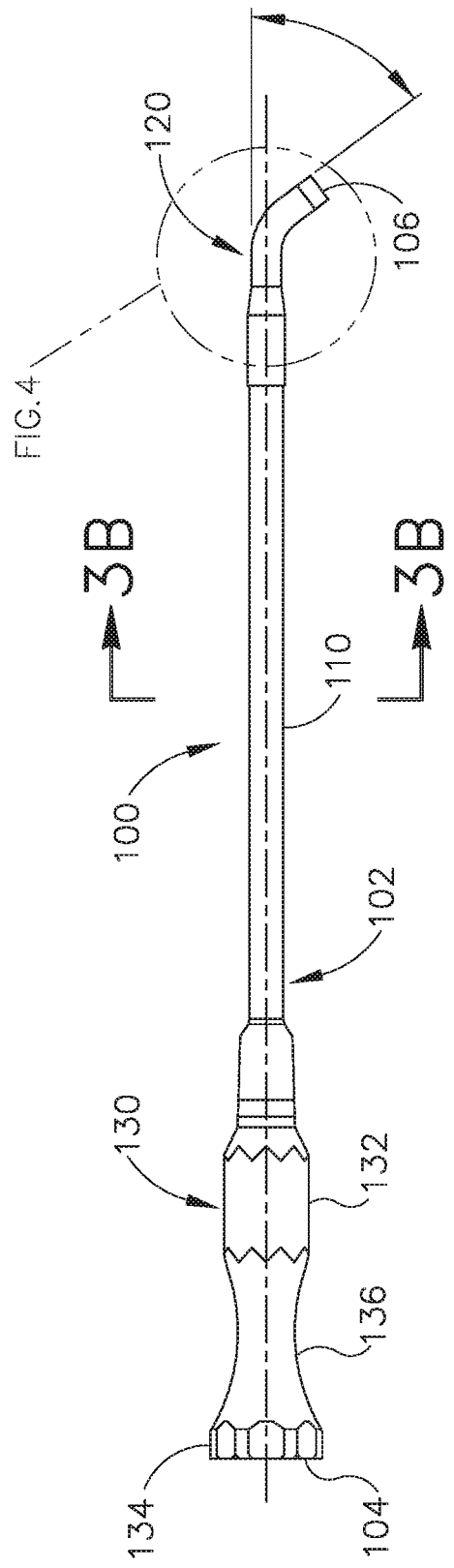
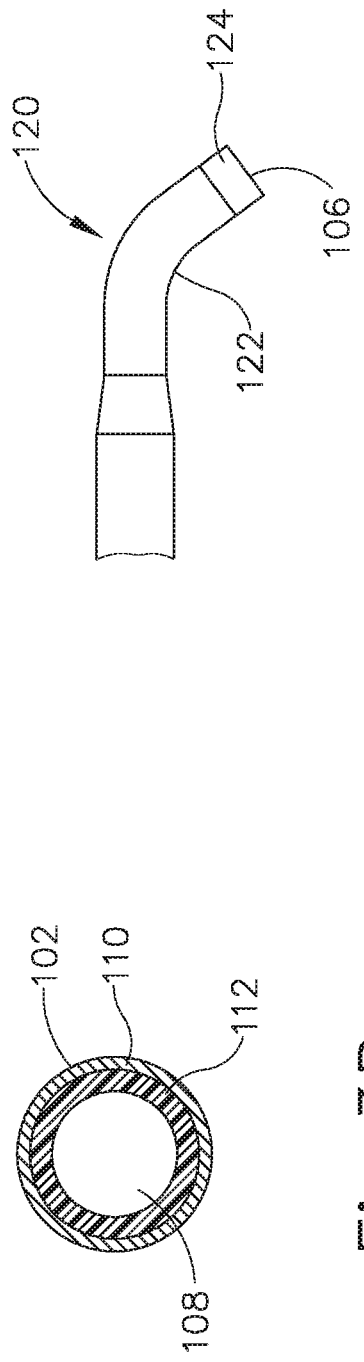
Fig. 3A
Fig. 3B
Fig. 4

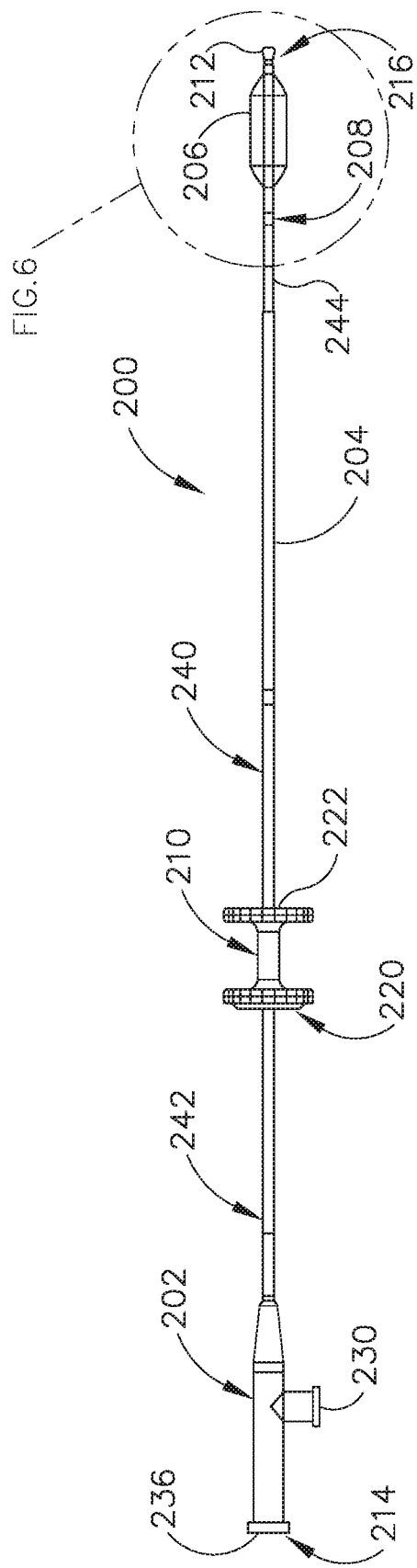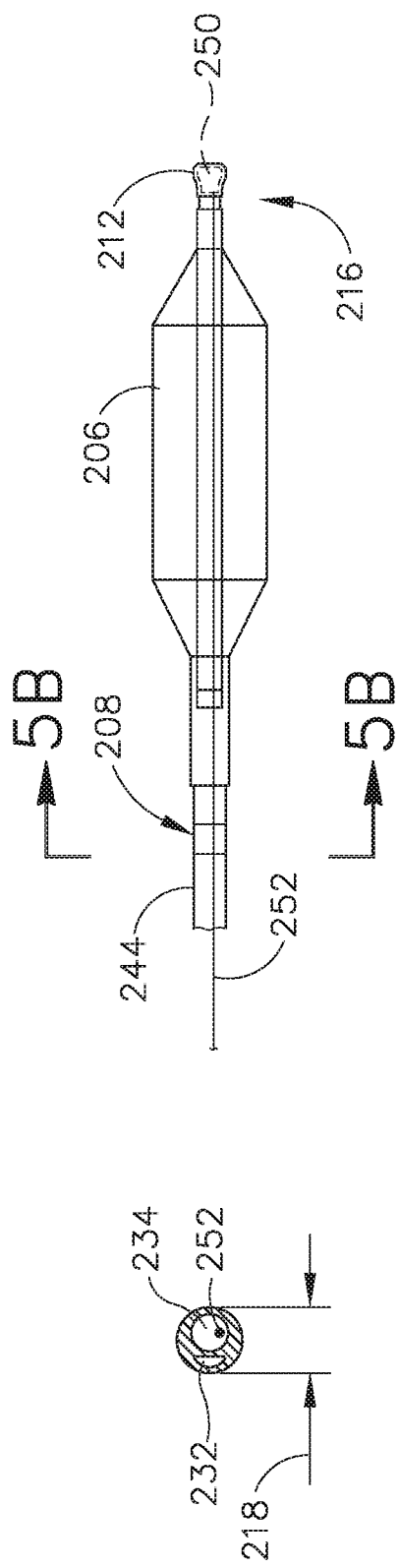

DILATION CATHETER WITH NAVIGATION SENSOR AND VENT PASSAGEWAY IN TIP

BACKGROUND

Referring to FIGS. 1-2, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow channel, of approximately 1.5 inches in length, that connects the middle ear (14) with the nasopharynx (30), which is the upper throat area just above the palate, in back of the nose. The ET (26) has narrowed distal portion (29) (referred to as the isthmus), that opens to the middle ear (14). The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This occurs frequently in children in connection with an upper respiratory infection and accounts for the hearing impairment associated with this condition.

A lining membrane (mucous membrane) of the middle ear (14) and ET (26) is connected with, and is the same as, the membrane of the nose (42), sinuses (44) and throat (32). Infection of these areas results in mucous membrane swelling which in turn may result in obstruction of the ET (26). This is referred to as serous otitis media, which as discussed above is essentially a collection of fluid in the middle ear (14). Serous otitis media can be acute or chronic, and may be the result of blockage of the pharyngeal ostium (28) of the ET (26), which leads to the accumulation of fluid in the middle ear (14). In the presence of bacteria, this fluid may become infected, leading to an acute suppurative otitis media (infected or abscessed middle ear). When infection does not develop, the fluid remains until the ET (26) again begins to function normally, at which time the fluid is absorbed or drains down the tube into the throat (32) through the ET (26) pharyngeal ostium (28).

Chronic serous otitis media may result from longstanding ET blockage, or from thickening of the fluid so that it cannot be absorbed or drained down the ET (26). This chronic condition may lead to hearing impairment. There may be recurrent ear pain, especially when the individual catches a cold. Fortunately, serous otitis media may persist for many years without producing any permanent damage to the middle ear mechanism. The presence of fluid in the middle ear (14), however, makes it very susceptible to recurrent acute infections. These recurrent infections may result in middle ear damage.

When the ET (26) contains a build-up of fluid, a number of things may occur. First, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Treatment of this condition with antihistamines and decongestants can take many weeks to be fully effective. Finally, the fluid can become infected, which can lead to pain, illness, and temporary hearing loss. If the inner ear (14) is affected, the patient may feel a spinning or turning sensation (vertigo). The infection may be treated with antibiotics.

However, even if antihistamines, decongestants, and antibiotics are used to treat an infection or other cause of fluid build-up in the middle ear (14), these treatments may not immediately resolve the pain and discomfort caused by the buildup of fluid in the middle ear (14). The most immediate relief may be felt by the patient if the fluid can be removed from the ET (26).

Antibiotic treatment of middle ear infections may result in normal middle ear function within three to four weeks. During the healing period, the patient can experience varying degrees of ear pressure, popping, clicking and fluctuation of hearing, occasionally with shooting pain in the ear. Resolution of the infection may leave the patient with uninfected fluid in the middle ear (14), localized in the ET (26).

Fluid build-up caused by these types of infections may be treated surgically. The primary objective of surgical treatment of chronic serous otitis media may be to reestablish ventilation of the middle ear, keeping the hearing at a normal level and preventing recurrent infection that might damage the eardrum membrane and middle ear bones. One method to opening the ET (26) includes the "Valsalva" maneuver, accomplished by forcibly blowing air into the middle ear (14) while holding the nose, often called popping the ear. This method may be effective for opening the ET (26) but it may not clear the accumulated fluid from the middle ear (14) and is essentially a temporary fix when fluid is present in the middle ear (14).

Methods for treating the middle ear (14) and the ET (26) include those disclosed in U.S. Pat. Pub. No. 2010/0274188, entitled "Method and System for Treating Target Tissue within the ET," published on Oct. 28, 2010, now abandoned, the disclosure of which is incorporated by reference herein; U.S. Pat. Pub. No. 2013/0274715, entitled "Method and System for Eustachian Tube Dilation," published on Oct. 17, 2013, now abandoned, the disclosure of which is incorporated by reference herein; and U.S. Pat. Pub. No. 2015/0374963, entitled "Vent Cap for a Eustachian Tube Dilation System," published on Dec. 31, 2015, issued as U.S. Pat. No. 10,350,396 on Jul. 16, 2019 the disclosure of which is incorporated by reference herein. As described in those references, functioning of the ET (26) may be improved by dilating the ET (26) with an expandable dilator instrument.

While a variety of surgical systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3A depicts a side elevational view of an exemplary guide catheter that may be used to position the dilation catheter of FIG. 5A;

FIG. 3B depicts a sectional view of the guide catheter shown in FIG. 3A, taken along line 3B-3B of FIG. 3A;

FIG. 4 depicts an enlarged view of the distal portion of the guide catheter shown in FIG. 3A;

FIG. 5A depicts a side elevational view of a balloon dilation catheter that may be used with the guide catheter of FIG. 3A;

FIG. 5B depicts a sectional view of the balloon dilation catheter shown in FIG. 5A, taken along line 5B-5B of FIG. 6;

FIG. 6 depicts an enlarged view of the distal end of the balloon dilation catheter shown in FIG. 5A;

Figure 1:
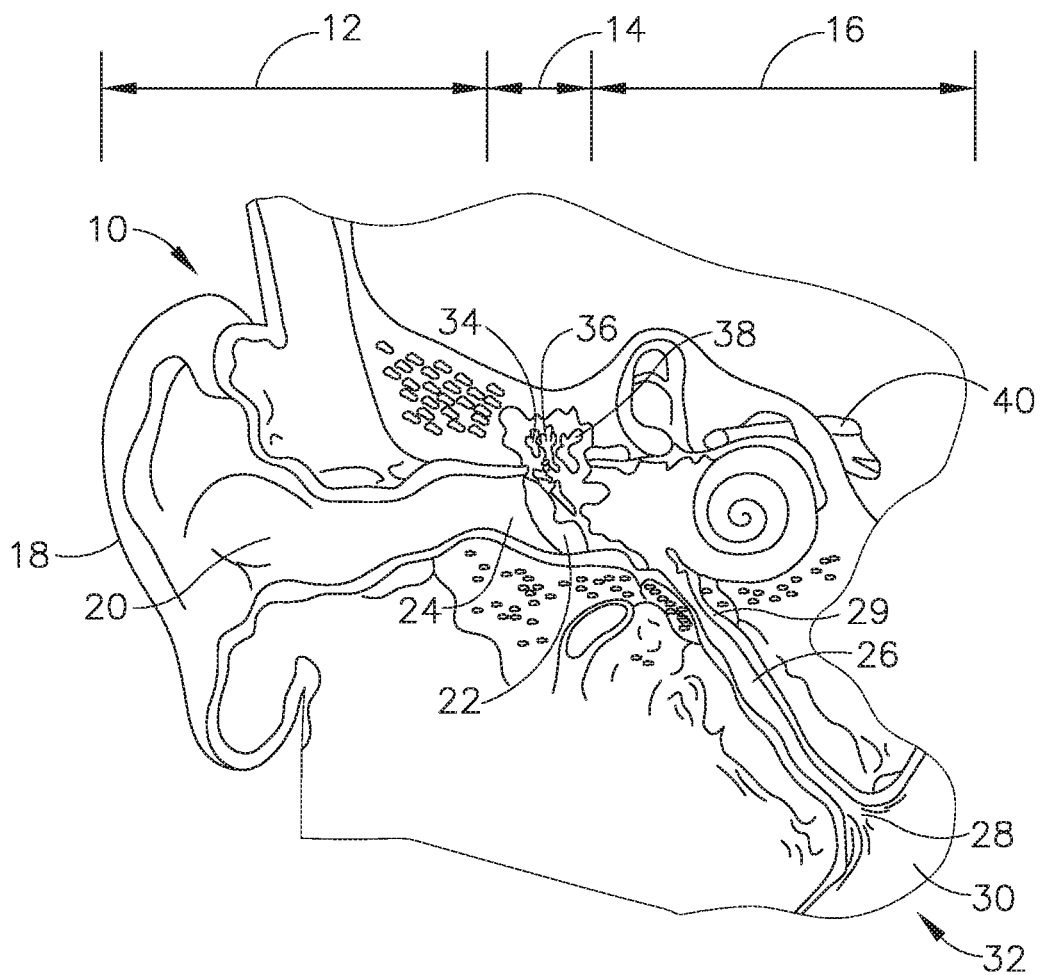
FIG. 1 depicts a schematic sectional view of a human ear showing the inner, middle, and outer ear portions, and the Eustachian tube connecting the middle ear with the nasopharynx region of the throat.
Figure 2:
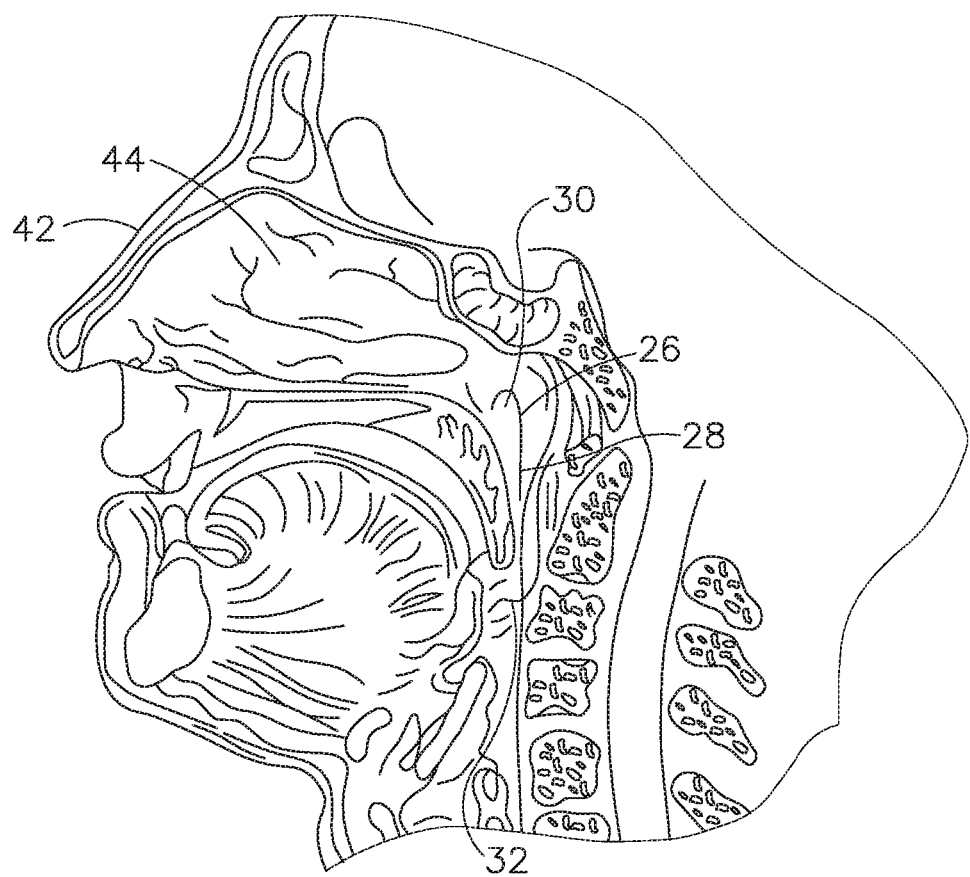
FIG. 2 depicts a schematic side sectional view of a human head showing the nasopharynx region of the throat illustrated in FIG. 1 containing the pharyngeal ostium of the Eustachian tube illustrated in FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention, it being understood, however, that this invention is not limited to the precise arrangements shown.

DETAILED DESCRIPTION

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

As used herein, the terms "about" and "approximately" for any numerical values or ranges indicate a suitable dimensional tolerance that allows the part or collection of components to function for its intended purpose as described herein.

I. Exemplary Eustachian Tube Dilation Catheter System

One example of a treatment that may be performed to treat an ET (26) that does not provide sufficient communication between the middle ear (14) and the pharyngeal ostium (28) includes accessing and dilating the ET (26) using a guide catheter (100) and a balloon dilation catheter (200), examples of which are shown in FIGS. 3A-6.

A. Exemplary Guide Catheter

Guide catheter (100) of the present example includes an elongate tubular shaft (102) that has a proximal end (104), a distal end (106) and a lumen (108) extending therebetween. Guide catheter (100) may have any suitable length, diameter, angle of bend, and location of the bend along the length of guide catheter (100), to facilitate accessing an ET (26) opening, such as the pharyngeal ostium (28). In some examples, guide catheter (100) may have a length between about 8 cm and about 20 cm, or more particularly between about 10 cm and about 15 cm, or more particularly about 11 cm.

FIG. 3B shows a sectional view of an elongate tubular shaft (102) of guide catheter (100). As can be seen, shaft (102) has an outer shaft tube (110), an inner shaft tube (112) and lumen (108). Outer shaft tube (110) may be constructed of a stiff material such as stainless steel and inner shaft tube (112) may be constructed of a more flexible material such as a polymeric material including but not limited to nylon and further including a PTFE liner. Lumen (108) may have a diameter of between about 2 mm and 3 mm, or more particularly between about 2.5 mm and about 2.6 mm, such that the balloon dilation catheter (200) can be easily inserted into lumen (108) for dilation of the ET (26). The combination of guide catheter (100) and balloon catheter (200) may present a compact system that is designed for a one-handed procedure. By "compact," it is intended that the length of the guide catheter shaft that is distal of the bend in the guide catheter is between about 0.5 and 2.0 about cm, in some versions between about 1 and about 2 cm, and in some versions about 1 cm. The compactness may help reduce interference with other instruments, such as an endoscope that may be used to help in visualizing the positioning of the system, as described below.

FIG. 4 shows an enlarged view of a distal portion (120) of guide catheter (100). Distal portion (120) may have a bend (122) with a bend angle that facilitates access into the ET (26) via the pharyngeal ostium (28). In various examples, the bend angle may be between about 45 degrees and about 65 degrees, and more specifically between about 50 degrees and about 60 degrees, such as about 55 degrees. Distal portion (120) of guide catheter (100) may be made of a transparent material, such as a polymer including but not limited to nylon and PTFE, such that balloon dilation catheter (200) is visible through distal portion (120) and such that distal portion (120) is more flexible than the elongate shaft (102). A distal tip (124) of distal portion (120) may be made of PEBAX® (polyether block amide) such that it provides for atraumatic access to the ET (26), and may contain 20% barium sulfate or other similar radiopaque materials for visualizable access.

As shown in FIG. 3A, a proximal portion (130) of guide catheter (100) includes a proximal hub (132) that aids in insertion of dilation catheter (200) into the ET (26). Hub hub (132) has a larger diameter proximal end (134) and a smaller diameter middle section (136) to facilitate stabilization of guide catheter (100) in the nose, rotation of guide catheter (100), and insertion of dilation catheter (200), as will be described in further detail below. Hub (132) is ergonomically designed for insertion, location, and rotation through slight manipulations with one hand.

B. Exemplary Balloon Dilation Catheter

FIGS. 5A-6 show details of balloon dilation catheter (200). In the present example, balloon dilation catheter (200) generally includes a proximal connector (202), an elongate shaft (204) extending distally from connector (202), and an expandable element in the form of a balloon (206) arranged on shaft (204). Proximal connector (202) defines a proximal end (214) of dilation catheter (200), and shaft (204) defines a distal end (216) of dilation catheter (200).

Balloon (206) is disposed on a distal shaft portion of dilation catheter shaft (204), proximally of distal end (216). Balloon (206) may be a polymer balloon (compliant, semi-compliant, or non-compliant). In some versions, balloon (206) comprises a suitable non-compliant material such as but not limited to polyethylene terephthalate (PET), PEBAX® (polyether block amide), nylon, or the like. Balloon (206) may be of any suitable size, including but not limited to sizes of 2 mm to 8 mm in diameter (when inflated), such as between about 5 mm and 6 mm, and sizes of 12 mm to 24 mm in working length. Exemplary inflated diameter and working length combinations of balloon (206) include, but are not limited to, the following (displayed as [inflated diameter]×[working length]): 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm. Balloon dilation catheter (200) includes a proximally located balloon inflation port (230) for inflating/activating balloon (206) by communicating a pressurized medium (e.g., saline) to balloon (206).

As shown best in FIG. 6, balloon dilation catheter (200) may further include a marker (208) arranged on the distal portion of shaft (204), at a location proximally of balloon (206). Marker (208) is positioned at a known distance from a proximal end of balloon (206), such that this distance may be used as a metric when positioning balloon (206) within an anatomical passageway in combination with an endoscope, such as endoscope (400) described below. In other versions, marker (208) may be omitted from shaft (204) and balloon (206) may be positioned within the passageway using other suitable methods, such as the exemplary methods described below in connection with navigation sensor (250) and variations thereof.

As shown in FIG. 5A, balloon dilation catheter (200) further includes an actuator (210) having a proximal side (220) and a distal side (222). Actuator (210) is fixed axially and rotationally to shaft (204), for example with an adhesive, and is configured to be manipulated by a physician to translate balloon dilation catheter (200) proximally and distally relative to guide catheter (100). Actuator (210) allows for easy, ergonomic one-handed advancement of dilation catheter (200) relative to guide catheter (100). It will be appreciated that actuator (210) may be by a physician using a thumb, an index finger, or any convenient combination of fingers (e.g., the index and middle fingers) or thumb and fingers.

A shaft portion (240) of elongate shaft (204) arranged distally of actuator (210) is sufficiently stiff to be guided through the nasal cavity and into the ET (26). Stiff shaft portion (240) may be constructed of stainless steel, and may include stainless steel hypotube, for example. A first flexible shaft portion (242) arranged proximally of actuator (210), as well as a second flexible shaft portion (244) arranged distally of stiff shaft portion (240), are more flexible than stiff shaft portion (240). In some examples, flexible shaft portions (242, 244) may be constructed of a polymeric material including but not limited to PEBAX® (polyether block amide). Flexible shaft portions (242, 244) enable dilation catheter (200) to accommodate endoscope (400) alongside catheter shaft (204) within a nasal passage as endoscope (400) is advanced distally through the nasal passage.

Distal end (216) of balloon dilation catheter (200) includes a distal tip (212) arranged at a distal end of catheter shaft (204), distally of balloon (206). Distal tip (212) may be constructed of a polymeric material including but not limited to PEBAX® (polyether block amide). As shown best in FIG. 6, tip (212) of the present example has a bulbous, blueberry-like shape that is atraumatic to tissue. Tip (212) may be approximately 1.5 mm to 2 mm in length, with an outer diameter of approximately 2 mm to 3 mm. The smoothness and roundness of tip (212) facilitates advancement of the balloon catheter (200) by helping tip (212) glide smoothly through the ET (26). The bulbous configuration of tip (212) enables tip (212) to function as a safety stop that prevents unwanted advancement of catheter (200) distally beyond the ET isthmus (29), which has a diameter of approximately 1 mm, into the middle ear (14) shown in FIG. 1. In that regard, tip (212) has a maximum outer diameter that is larger than the diameter of the isthmus (29), and also larger than portions of catheter shaft (204) located proximally and distally of balloon (206), such as shaft diameter (218) shown in FIG. 5B. Accordingly, tip (212) is configured to prevent the balloon catheter (200) from passing distally through the isthmus (29) and into the middle ear (14), which could otherwise cause damage to auditory structures located within the middle ear (14).

As shown in the sectional view of FIG. 5B, first and second lumen (232, 234) extend longitudinally through balloon dilation catheter (200). Lumen (232, 234) extend side-by-side, but are separated from one another by an interior wall. In the present example, first lumen (232) is in the form of an inflation lumen, and second lumen (234) is in the form of a working lumen. Inflation lumen (232) communicates proximally with inflation connection (230) and distally with an interior of balloon (206). Inflation lumen (232) is configured to direct an inflation fluid between inflation port (230) and balloon (206) for selectively expanding and collapsing balloon (206). Inflation fluid may comprise water, saline, or a contrast medium, for example. The internal pressure to which balloon (206) is inflated may be approximately 3 to 15 atmospheres, and more specifically approximately 6 to 12 atmospheres, for example. Further, inflation fluid may be directed into and withdrawn from the interior of balloon (206) using any suitable mechanism, such as a mechanism of the type disclosed in U.S. Pat. Pub. No. 2017/0119414, entitled "Fluid Communication Features for Eustachian Tube Dilation Instrument," published on May 4, 2017, issued as U.S. Pat. No. 10,034,681 on Jul. 31, 2018, the disclosure of which is incorporated by reference herein.

Working lumen (234) communicates proximally with open proximal end (214) of dilation catheter (200) defined by proximal connector (202), and distally with an opening formed at distal end (216), as described in greater detail below. Working lumen (234) is configured to slidably receive a guidewire therethrough, such as guidewire (500) shown in FIGS. 10A and 10B. Working lumen (234) also accommodates a sensor wire (252) of a navigation sensor (250) arranged within distal tip (212), as described below. As shown in FIG. 5B, sensor wire (252) is offset from a central axis of working lumen (234) to avoid interference with guidewire (500).

Working lumen (234) is also configured to permit passage of fluid therethrough, between proximal and distal ends (214, 216). Such fluid may comprise air, for example to enable a pressure equalization between ET (26) and the ambient atmosphere during an ET dilation procedure. In this manner, open distal end (216) of dilation catheter (200) is configured to function as a vent passageway. Such fluid may also comprise an irrigation fluid or other therapeutic substance, such as a medicament, that is injected distally through working lumen (234) to a treatment site within the patient. Non-limiting examples of therapeutic substances and other injection fluids that may be delivered through working lumen (234) to a treatment site within a patient may include one or more of those described in U.S. Pat. Pub. No. 2017/0119414, issued as U.S. Pat. No. 10,034,681 on Jul. 31, 2018, the disclosure of which is incorporated by reference above.

Injection fluid is delivered to working lumen (234) through an injection port (236) of proximal connector (202), defined at proximal end (214). Injection port (236) and inflation port (230) may be provided with distinct types of connecting features, to ensure that ports (230, 236) are not confused with one another during use. For example, one port (230, 236) may include a female connecting feature, while the other port (230, 236) includes a male connecting feature. Additionally, or in the alternative, one port (230, 236) may include a right-handed thread while the other port (230, 236) includes a left-handed thread, for example.

As shown schematically in FIG. 6, balloon dilation catheter (200) further includes a navigation sensor (250) arranged at a distal end of catheter shaft (204). In the present example, navigation sensor (250) is arranged radially inwardly of an exterior of (or "within") distal tip (212). As described in greater detail below, navigation sensor (250) is in the form of an electromagnetic sensor and is configured to generate a signal corresponding to a location of distal tip (212) within a patient during a surgical procedure. A signal transmission wire (252) extends longitudinally through dilation catheter (200), for example through working lumen (234). Wire (252) is coupled at its distal end to navigation sensor (250), and communicates at its proximal end with a signal receiving device, such as processor (606) described below. Wire (252) is configured to transmit the signal generated by navigation sensor (250) proximally to the signal receiving device, which in turn is configured to interpret the signal to inform a physician of the location of the distal tip (212) within the patient in real-time during the surgical procedure. Accordingly, navigation sensor (250) facilitates accurate positioning of dilation catheter (200) within the patient during a treatment procedure, as described below.

C. Exemplary Alternative Guide Catheter

Figure 7:
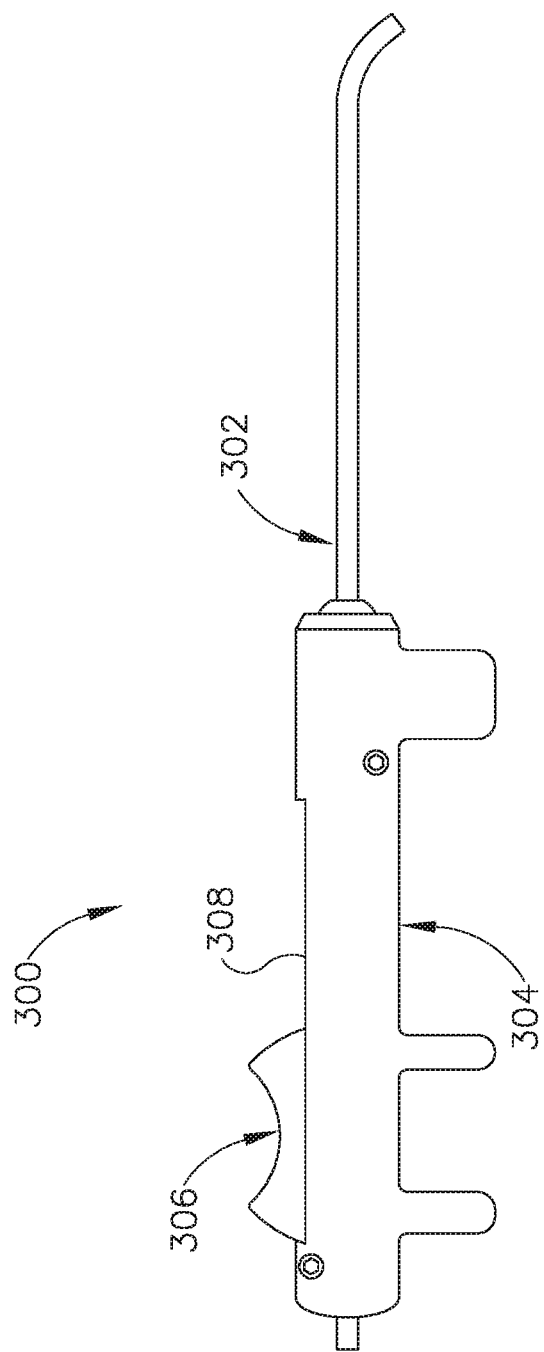
FIG. 7 depicts a side elevational view of another exemplary guide catheter that may be used to position the dilation catheter of FIG. 5A.

FIG. 7 shows another exemplary guide catheter (300). In this example, proximal hub (132) is replaced with a handle (304). Guide catheter (300) comprises an elongate shaft (302) and a handle (304) to aid in insertion of a balloon dilation catheter, such as balloon catheter (200), into the ET (26) in a manner similar to that described below with regard to guide catheter (200). In the example shown in FIG. 7, an actuator (306) in the form of a slider is attached to portion of balloon catheter (200) that is contained within handle (304) and is slidably contained within elongate shaft (302) of guide catheter (300). Actuator (306) is thus slidable relative to handle (304) along a channel (308) to thereby selectively advance and retract balloon catheter (200) relative to elongate shaft (302). In use, elongate shaft (302) is inserted distally into the nasal cavity of the patient and balloon catheter (200) is advanced distally into the ET (26) by a physician by advancing actuator (302) distally along channel (308) using thumb or single finger, for example. Distal advancement of balloon catheter (200) may be continued until: (i) a visual marker indicates that advancement is complete; (ii) enlarged distal tip (212) of balloon catheter (200) abuts the isthmus (29) of the ET (26), thereby indicating that distal advancement is complete; or (iii) actuator (302) abuts a distal end of channel (308), thereby indicating that distal advancement is complete.

D. Exemplary Endoscope

Figure 8:
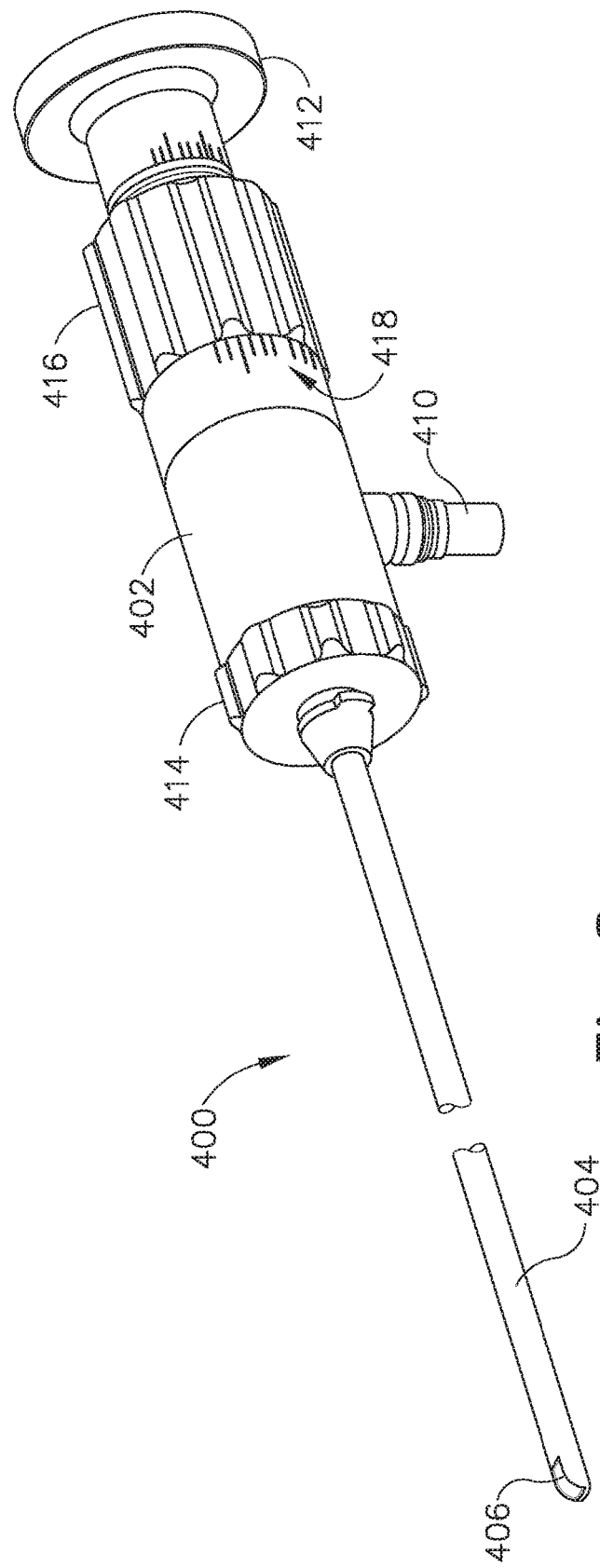
FIG. 8 depicts a perspective view of an exemplary endoscope suitable for use with the guide catheter of FIG. 3A and/or the balloon dilation catheter of FIG. 5A.
Figure 9:
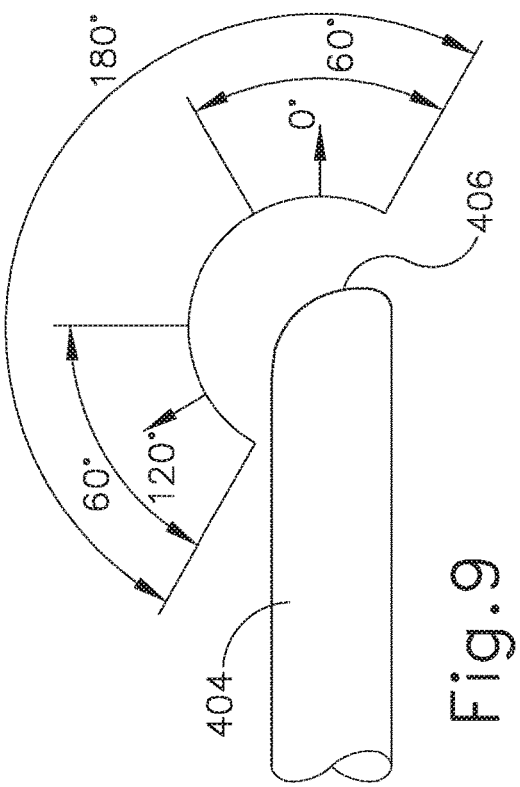
FIG. 9 depicts a side elevational view of the distal end of the endoscope of FIG. 8, showing an exemplary range of viewing angles.

FIGS. 8 and 9 show an exemplary endoscope (400). Endoscope (400) is configured to provide visualization within an anatomical passageway (e.g., within the oro-nasal cavity, etc.) during a dilation procedure using balloon dilation catheter (200) and one of guide catheters (100, 300), for example as described below in connection with FIGS. 10A and 10B.

Endoscope (400) of the present example comprises a body (402) and a rigid shaft (404) extending distally from body (402). The distal end of shaft (404) includes a curved transparent window (406). A plurality of rod lenses and light transmitting fibers (not shown) may extend along the length of shaft (404). A lens (not shown) is positioned at the distal end of the rod lenses, and a swing prism (not shown) is positioned between the lens and window (406). The swing prism is pivotable about an axis that is transverse to the longitudinal axis of shaft (404). The swing prism defines a line of sight that pivots with the swing prism. The line of sight defines a viewing angle relative to the longitudinal axis of shaft (404). This line of sight may pivot from approximately 0 degrees to approximately 120 degrees, from approximately 10 degrees to approximately 90 degrees, or within any other suitable range. The swing prism and window (406) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. It will be understood that these values are provided merely as examples.

Endoscope body (402) of the present example includes a light post (410), an eyepiece (412), a rotation dial (414), and a pivot dial (416). Light post (410) is in communication with the light transmitting fibers in shaft (404) and is configured to couple with a source of light, to thereby illuminate the site in the patient distal to window (406). Eyepiece (412) is configured to provide visualization of the view captured through window (406) via the optics of endoscope (400). It should be understood that a visualization system (e.g., camera and display screen, etc.) may be coupled with eyepiece (412) to provide visualization of the view captured through window (406) via the optics of endoscope (400). Rotation dial (414) is configured to rotate shaft (404) relative to body (402) about the longitudinal axis of shaft (404). It should be understood that such rotation may be carried out even while the swing prism is pivoted such that the line of sight is non-parallel with the longitudinal axis of shaft (404). Pivot dial (416) is coupled with the swing prism and is thereby operable to pivot the swing prism about the transverse pivot axis. Indicia (418) on body (402) provides visual feedback indicating the viewing angle. Various suitable components and arrangements that may be used to couple rotation dial (414) with the swing prism will be apparent to those of ordinary skill in the art in view of the teachings herein.

By way of example only, endoscope (400) may be configured in accordance with at least some of the teachings of U.S. Pat. Pub. No. 2010/0030031, entitled "Swing Prism Endoscope," published on Feb. 4, 2012, now abandoned, the disclosure of which is incorporated by reference herein. In some versions, endoscope (400) is configured similar to the Acclarent Cyclops™ Multi-Angle Endoscope by Acclarent, Inc. of Menlo Park, Calif. Other suitable forms that endoscope (400) may take will be apparent to those of ordinary skill in the art in view of the teachings herein.

E. Exemplary Method of Treating the Eustachian Tube

Figure 10A:
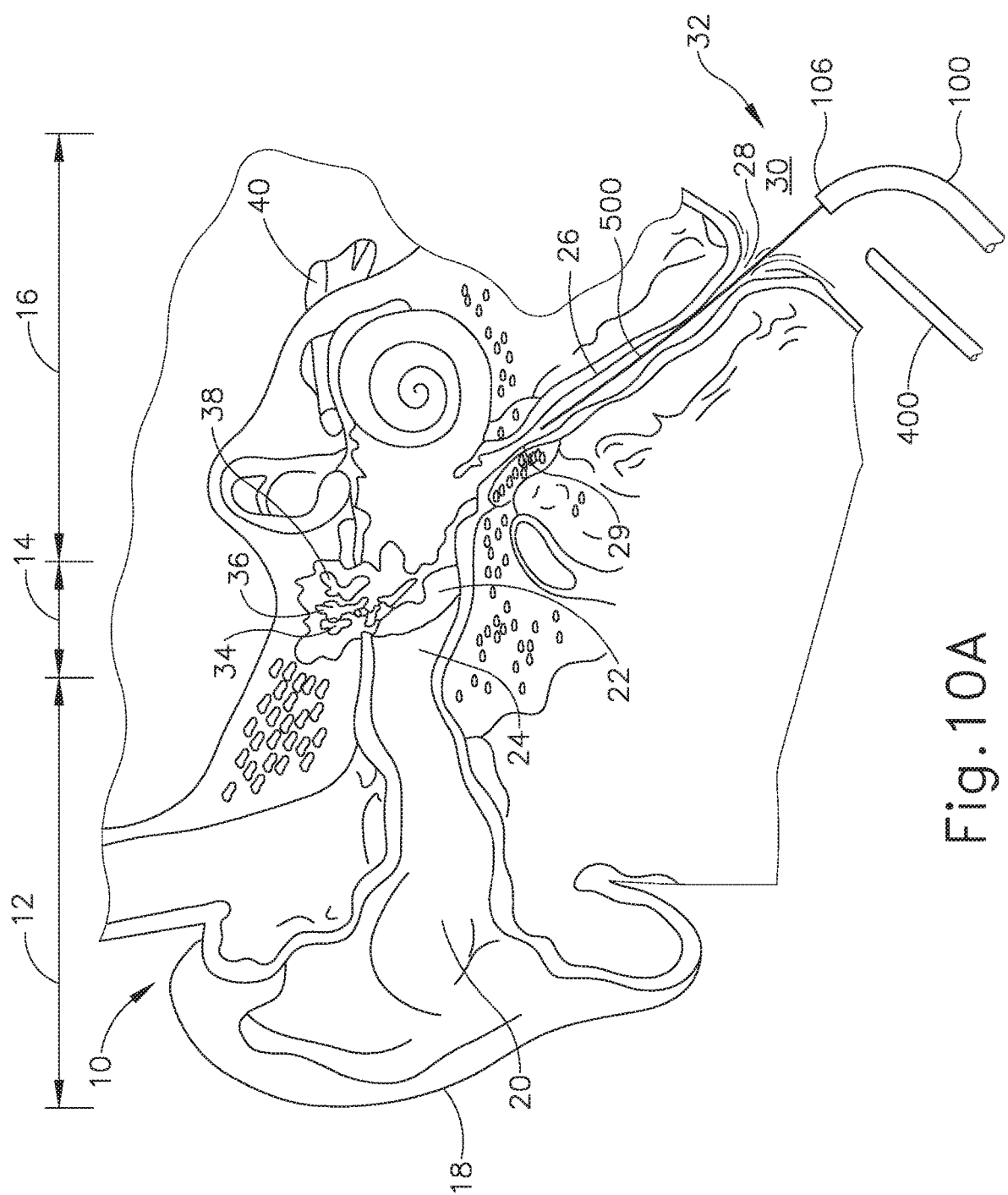
FIG. 10A depicts a schematic sectional view of a guide catheter, a balloon catheter, and an endoscope being positioned in relation to a Eustachian tube of a patient, with a guidewire disposed in the Eustachian tube.
Figure 10B:
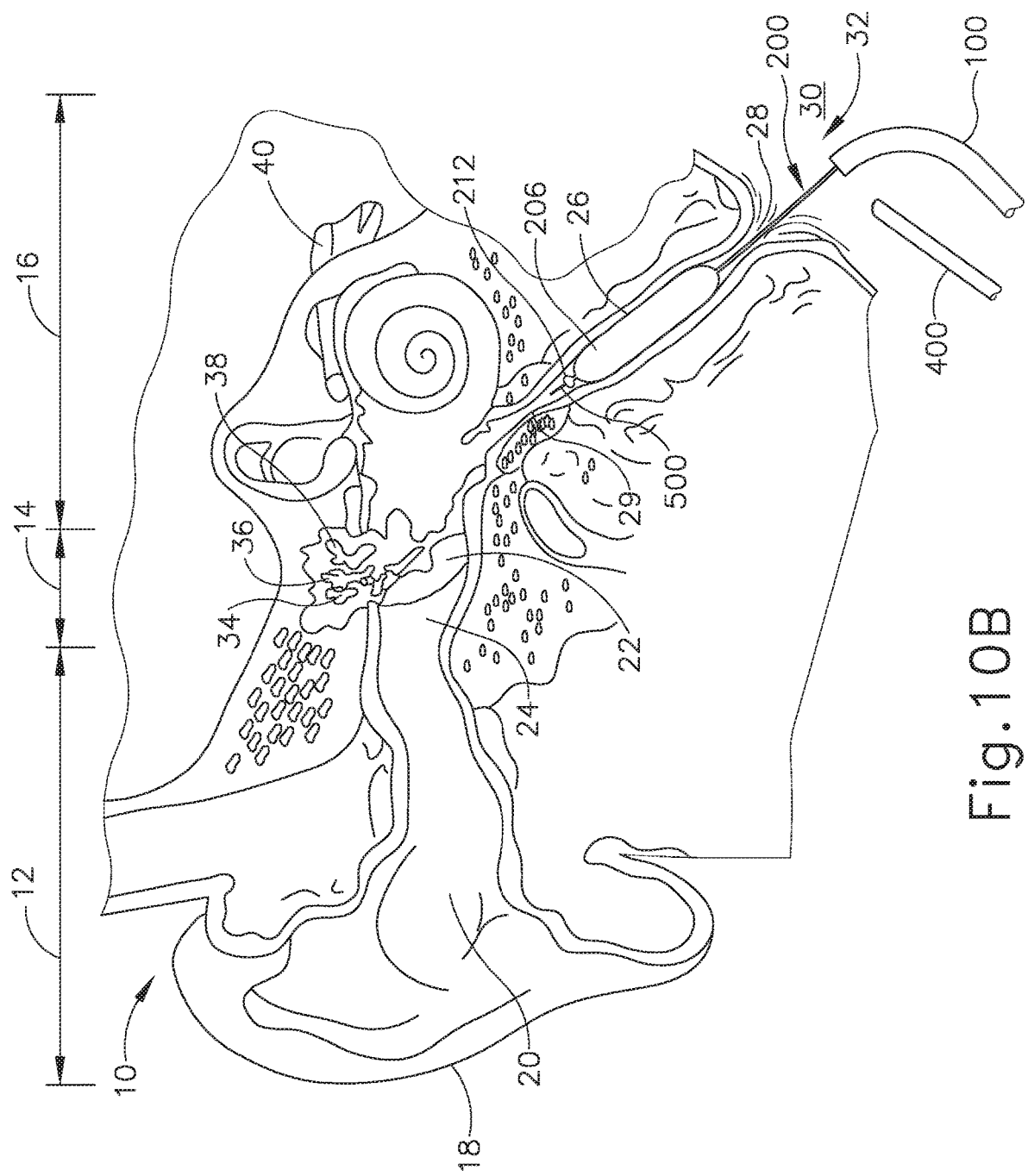
FIG. 10B depicts a schematic sectional view of the guide catheter, balloon catheter, and endoscope of FIG. 10A, with a balloon of the balloon catheter being expanded to dilate the Eustachian tube.

FIGS. 10A and 10B schematically show an exemplary procedure for treating the ET (26) using the exemplary features described above. While the steps are shown in connection with guide catheter (100), it will be appreciated that they may also be performed using guide catheter (300). As shown in FIG. 10A, guide catheter (100) is advanced distally into a nostril and through the nasal cavity of a patient to position distal end (106) of the guide catheter (100) at or near the pharyngeal ostium (28), which opens distally to the ET (26). In some instances, guide catheter (100) may be passed distally through a nostril to the ET (26) on the ipsilateral (same side) of the head. In some other instances, guide catheter (100) may be passed distally through a nostril to the ET (26) on the contralateral (opposite side) of the head. A guidewire (500) or other suitable guiding element, such as an illuminating fiber, may be used to aid in accessing the ET (26). In some versions, guidewire (500) may be omitted. Additionally, endoscope (400) may be employed to facilitate positioning of guide catheter (100), by providing the physician with an image of guide catheter distal end (106) relative to surrounding anatomical structures, including pharyngeal ostium (28).

As shown in FIG. 10B, after guide catheter (100) is in a desired position relative to pharyngeal ostium (28), balloon dilation catheter (200) is advanced distally through guide catheter (100) to position balloon (206) within the ET (26). For example, the physician may place their index and middle fingers on either side of the smaller diameter middle section (136) of proximal hub (132) of guide catheter (100). The physician will then place their thumb on the proximal side (220) of actuator (210), or between both sides (220, 222) of actuator (210), and will use their thumb to slide balloon dilation catheter (200) distally through guide catheter (100) to position balloon (206) within the ET (26). Alternatively, the physician may grasp proximal hub (132) of guide catheter (100) and use their index finger placed on actuator (210) to advance balloon catheter (200) distally.

As described above, bulbous distal tip (212) of balloon dilation catheter (200) prevents dilation catheter (200) from advancing past the isthmus (29) and into the middle ear (14), which could otherwise cause injury to the patient. Further, distal side (222) of actuator (210) will bottom out against proximal end (104) of guide catheter (100), such that the balloon catheter (200) cannot advance distally any further. Actuator (210) thus prevents balloon catheter (200) from advancing past the isthmus (29).

In an alternative example, balloon catheter (200) is advanced distally into a nostril of the patient, and balloon (206) is positioned within the ET (26), without use of a guide catheter (100, 300). In such cases, the physician will advance the balloon catheter (200) distally until proximal side (220) of actuator (210) is adjacent to the patient's nostril. Distal side (222) of the actuator (210) will bottom out against the patient's nostril, such that balloon catheter (200) cannot advance distally any further. In this manner, actuator (210) prevents balloon catheter (200) from advancing past the isthmus (29) and reaching the middle ear (14). It will be understood that actuator (210) may be positioned at the appropriate distance along elongate shaft (204) of balloon catheter (200) such that access to the ET (26) may be performed from the contralateral or the ipsilateral side.

Any number of procedures may be carried out following placement of balloon dilation catheter (200) in the desired position as described above. For instance, as shown in FIG.

10B, the ET (26) may be dilated by directing inflation fluid to balloon (206) and thereby inflating balloon (206) as described above. In some instances, balloon (206) may carry an expandable stent (not shown) for delivery into the ET (26) upon expansion of balloon (206). In addition, or alternatively, to the dilation of the ET (26), the isthmus (29) may be flushed and/or otherwise treated with an injected substance as described above, and/or as described in U.S. Pat. Pub. No. 2016/0287445, entitled "Method and Apparatus for Cleaning Isthmus of Eustachian Tube," published on Oct. 6, 2016, issued as U.S. Pat. No. 10,335,319 on Jul. 2, 2019, the disclosure of which is incorporated by reference herein. Following treatment of the ET (26), balloon (206) is deflated (if previously inflated) and dilation catheter (200) is withdrawn proximally from the patient. Following treatment, the ET (26) will resume normal functioning, opening and closing to equalize atmospheric pressure in the middle ear (14) and to protect the middle ear (14) from unwanted pressure fluctuations and loud sounds.

II. Exemplary Image Guided Navigation System

A. Overview of Image Guided Navigation System

Figure 11:
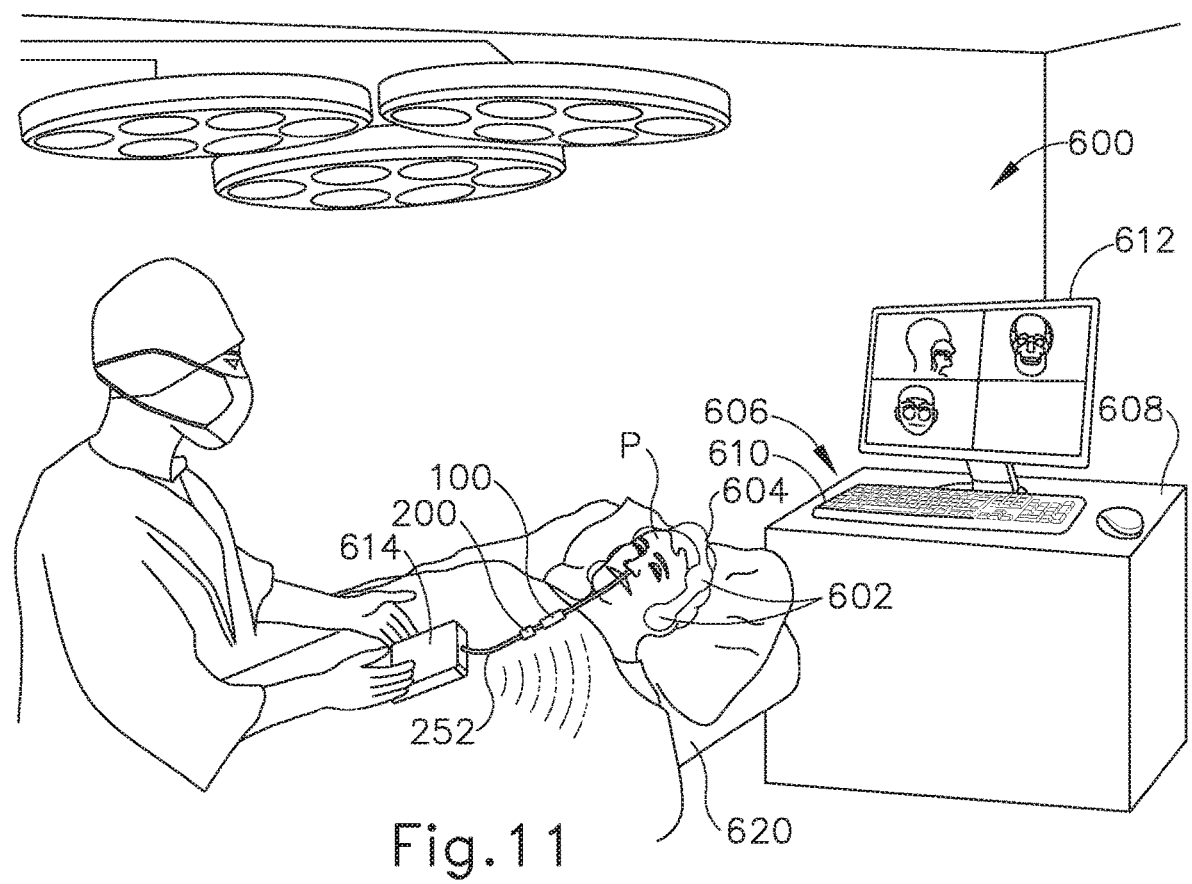
FIG. 11 depicts a schematic perspective view of an exemplary image-guided surgery navigation system, incorporating the guide catheter of FIG. 3A and the balloon dilation catheter of FIG. 5A, being implemented during a surgical procedure on a patient.
Figure 12:
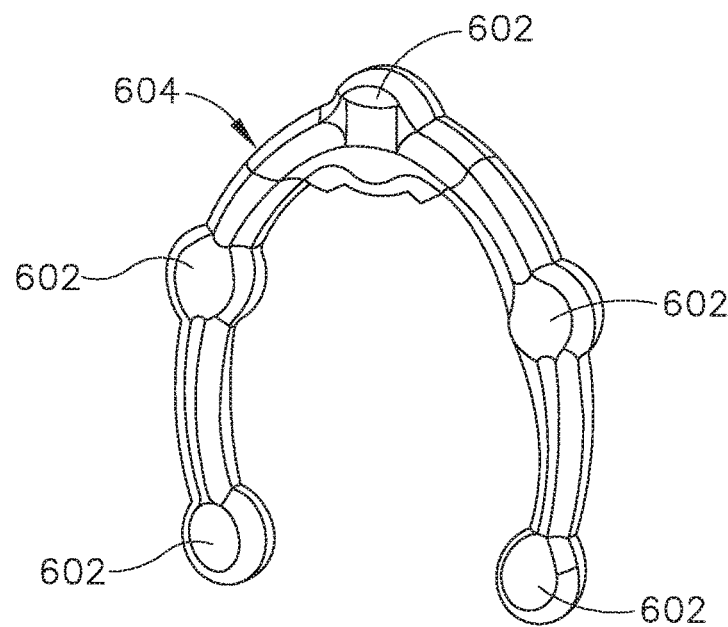
FIG. 12 depicts a perspective view of a frame component of the image-guided surgery navigation system of FIG. 11.

FIGS. 11 and 12 show an exemplary image-guided surgery (IGS) navigation system (600) configured to performed a Eustachian tube (ET) treatment procedure on a patient (P). As described in greater detail below, IGS navigation system (600) includes a computer used to obtain a real-time correlation of the location of an instrument that has been inserted into the patient's body, such as balloon dilation catheter (200), to a set of preoperatively obtained images (e.g., a CT or MRI scan, 3-D map, etc.) so as to superimpose the current location of the instrument on the preoperatively obtained images. In some instances, a digital tomographic scan (e.g., CT or MRI, 3-D map, etc.) of the operative field is obtained prior to surgery. A specially programmed computer is then used to convert the digital tomographic scan data into a digital map. During surgery, an instrument having one or more sensors (e.g., electromagnetic coils that emit electromagnetic fields and/or are responsive to externally generated electromagnetic fields) mounted thereon is used to perform the procedure while the sensors send data to the computer, indicating the current position of the surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real-time position of the surgical instrument relative to the anatomical structures shown in the scan images. In this manner, the surgeon is able to know the precise position of the sensor-equipped instrument by viewing the video monitor, even if the surgeon is unable to directly visualize the instrument itself at its current location within the body.

IGS navigation system (600) incorporates balloon dilation catheter (200) described above, and may further incorporate a suitable guide catheter such as one of guide catheters (100, 300) described above. As described in greater detail below, IGS navigation system (600) is configured to implement navigation sensor (250) of dilation catheter (200) to provide real-time location tracking of distal end (216) of dilation catheter (200) within the patient (P) during a surgical procedure, and thereby facilitate accurate positioning of dilation catheter (200) within the patient (P). While IGS navigation system (600) is described below in connection with the positioning of balloon dilation catheter (200) and variations thereof within the ET (26), it will be appreciated that IGS navigation system (600) may also be employed in procedures for accessing and treating various other anatomical passageways of a patient with dilation catheter (200) and the variations thereof described below.

IGS navigation system (600) of the present example includes a set of magnetic field generators (602). Before a surgical procedure begins, field generators (602) are positioned about the head of the patient (P). As best shown in FIG. 12, in the present example field generators (602) arranged integrally within a frame (604) having a horseshoe-like shape and configured to be positioned about the patient's head. In the example of FIG. 11, patient (P) is positioned on a medical procedure table (620), and frame (604) is positioned above table (620) and about the patient's head. Frame (604) may be mounted to any suitable support structure (not shown), which may be coupled directly to medical procedure table (620) or provided independently from table (620), such as a floor-mounted stand. In other examples, frame (604) may be secured directly to the head of patient (P). It should be understood that field generators (602) may be positioned at various other suitable locations relative to patient (P), and on various other suitable structures.

Figure 14:
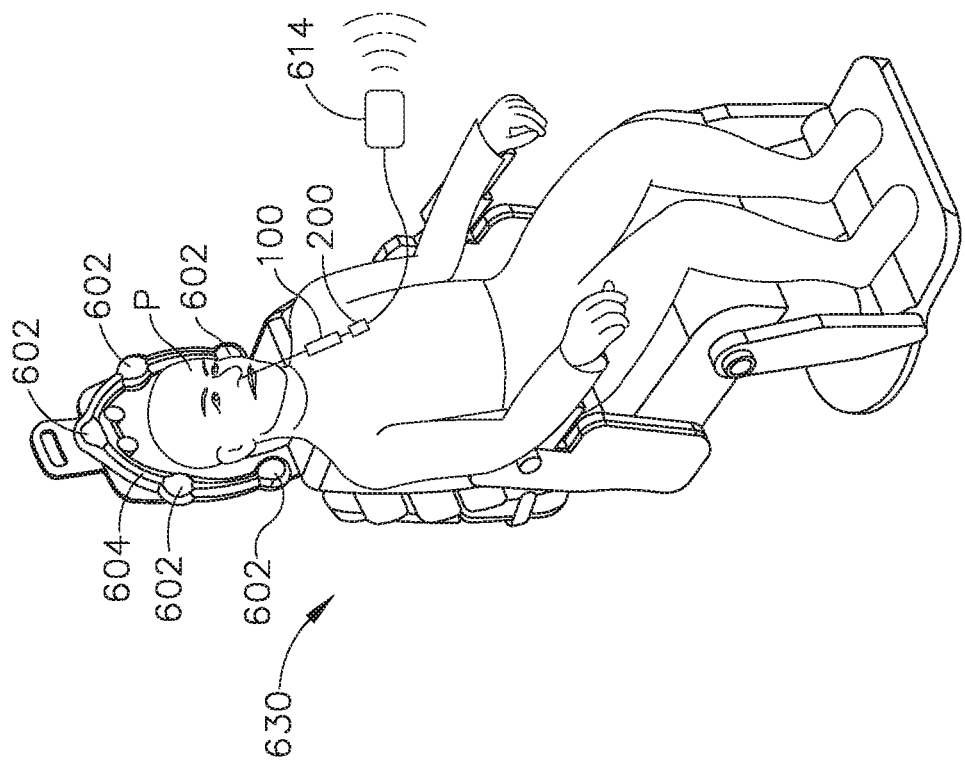
FIG. 14 depicts a perspective view of a patient seated in the medical procedure chair of FIG. 13, with the image-guided surgery navigation system of FIG. 11 being used to perform a procedure on the patient while seated in the chair.
Figure 13:
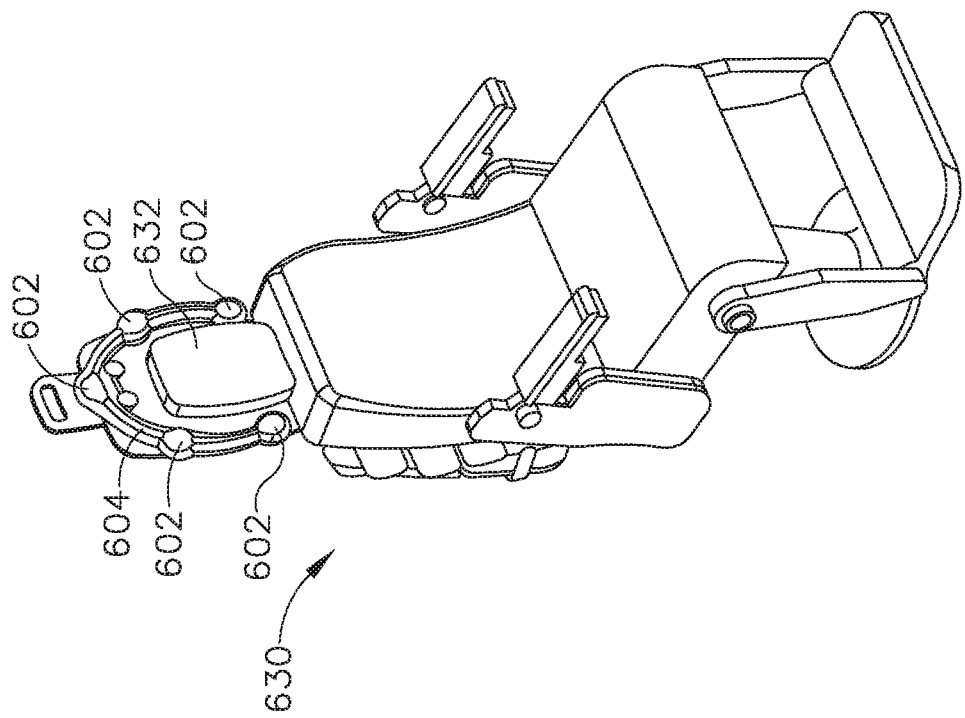
FIG. 13 depicts a perspective view of an exemplary medical procedure chair, with the frame component of the image-guided surgery navigation system of FIG. 12 mounted to the chair.

FIGS. 13 and 14 show another exemplary implementation of IGS navigation system (600), in which patient (P) is seated in a medical procedure chair (630). Frame (604) is mounted to a headrest (632) of chair (630) such that frame (604) extends about the head of patient (P) when seated in chair (630). Medical procedure chair (630) may be configured according to one or more teachings of U.S. Patent App. No. 62/555,824, entitled "Apparatus to Secure Field Generating Device to Chair," filed Sep. 8, 2017, the disclosure of which is incorporated by reference herein.

Field generators (602) of IGS navigation system (600) are operable to transmit alternating magnetic fields of different frequencies into a region in proximity to frame (604), and thereby generate an electromagnetic field in the region. In the present example, field generators (602) and frame (604) are arranged relative to the patient (P) such that the resulting electromagnetic field is formed about the patient's head. In other examples, field generators (602) and frame (604) may be suitably arranged in various other manners so as to generate an electromagnetic field about various other portions of the patient's body. Various suitable components that may be used to form and drive field generators (602) will be apparent to those of ordinary skill in the art in view of the teachings herein.

Field generators (602) enable tracking of the position of navigation sensor (250), and thus distal end (216), of balloon dilation catheter (200) when navigation sensor (250) moves through the electromagnetic field generated by field generators (602). In particular, as described in greater detail below, electromagnetic navigation sensor (250) of balloon dilation catheter (200) is configured to interact with the electromagnetic field and generate an electric signal in response to movement of sensor (250) through the electromagnetic field. Navigation sensor (250) then communicates this signal to a processor (606) of IGS navigation system (600). Processor (606), in turn, receives the signal and determines the three-dimensional location of navigation sensor (250), and catheter distal end (216) at which sensor (250) is arranged, within the electromagnetic field and thus the patient.

Processor (606) of IGS navigation system (600) comprises a processing unit that communicates with one or more memories, and is configured to control field generators (602) and other elements of IGS navigation system (600). In the present example, processor (606) is mounted in a console (608), which comprises operating controls (610) that include a keypad and/or a pointing device such as a mouse or trackball. A physician uses operating controls (610) to interact with processor (606) while performing the surgical procedure. Processor (606) uses software stored in a memory of processor (606) to calibrate and operate system (600). Such operation includes driving field generators (602), processing data received from navigation sensor (250), processing data from operating controls (610), and driving display screen (612). The software may be downloaded to processor (606) in electronic form, over a network, for example, or it may, alternatively or additionally, be provided and/or stored on non-transitory tangible media, such as magnetic, optical, or electronic memory.

Processor (606) is further operable to provide video in real time via display screen (612), showing the position of distal end (216) of balloon dilation catheter (200) in relation to a video camera image of the patient's head, a CT scan image of the patient's head, and/or a computer generated three-dimensional model of the anatomy within and adjacent to the patient's nasal cavity. Display screen (612) may display such images simultaneously and/or superimposed on each other. Moreover, display screen (612) may display such images during the surgical procedure. Such displayed images may also include graphical representations of instruments that are inserted in the patient's head, such as dilation catheter (200), such that the physician may view the virtual rendering of the instrument at its actual location in real time. Such graphical representations may look like the instrument or may be a much simpler representation such as a dot, crosshairs, etc. By way of example only, display screen (612) may provide images in accordance with at least some of the teachings of U.S. Pat. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the physician is simultaneously using an endoscope, such as endoscope (400) described above, the endoscopic image may also be provided on display screen (612). The images provided through display screen (612) may assist the physician in maneuvering and otherwise manipulating instruments within the patient's head.

Any suitable device may be used to generate a three-dimensional model of the internal anatomy of the portion of the patient's body (e.g., head) about which the electromagnetic field is generated and into which balloon dilation catheter (200) is to be inserted for conducting a treatment procedure. By way of example only, such a model may be generated in accordance with at least some of the teachings of U.S. Pat. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional anatomical model may be generated will be apparent to those of ordinary skill in the art in view of the teachings herein. It should also be understood that, regardless of how or where the three-dimensional model is generated, the model may be stored on console (608). Console (608) may thus render images of at least a portion of the model via display screen (612), and further render real-time video images of the position of distal end (216) of dilation catheter (200) in relation to the model via display screen (612).

In addition to connecting with processor (606) and operating controls (610), console (608) may also connect with other elements of IGS navigation system (600). For instance, as shown in FIG. 11, a communication unit (614) may be coupled with balloon dilation catheter (200) via wire (252), shown in FIG. 6. Communication unit (614) of this example is configured to provide wireless communication of data and other signals between console (608) and navigation sensor (250) of dilation catheter (200). In some versions, communication unit (614) simply communicates data or other signals from navigation sensor (250) to console (608) unidirectionally, without also communicating data or other signals from console (608). In some other versions, communication unit (614) provides bi-directional communication of data or other signals between navigation sensor (250) and console (608). While communication unit (614) of the present example couples with console (608) wirelessly, some other versions may provide wired coupling between communication unit (614) and console (608). Various other suitable features and functionality that may be incorporated into communication unit (614) will be apparent to those of ordinary skill in the art in view of the teachings herein.

In addition to, or in lieu of, having the components and operability described herein, IGS navigation system (600) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (600) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

B. Exemplary Externally Mounted Navigation Sensor

Figure 15:
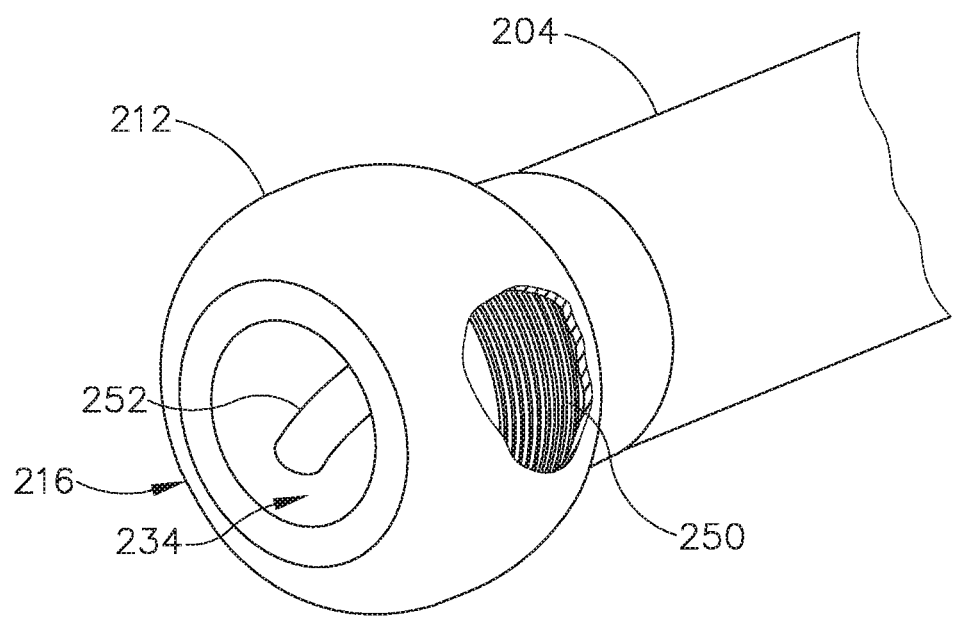
FIG. 15 depicts a perspective view of a distal end portion of the balloon dilation catheter of FIG. 5A.
Figure 16:
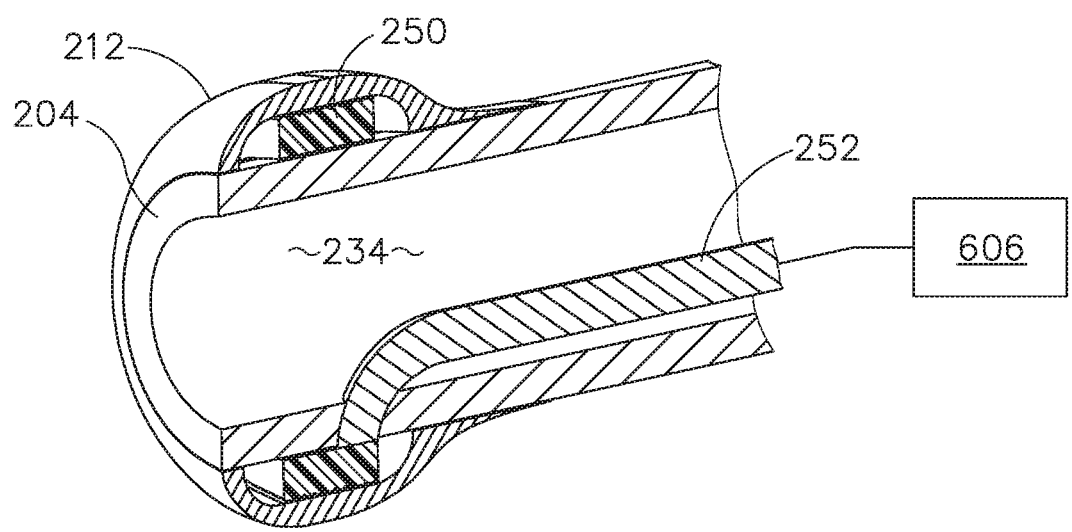
FIG. 16 depicts a side sectional view of the distal end portion of the balloon dilation catheter of FIG. 15.

FIGS. 15 and 16 show additional details of distal end (216) of balloon dilation catheter (200), at which bulbous distal tip (212) and navigation sensor (250) are arranged. The distal end portion of dilation catheter shaft (204) that defines distal end (212) may be referred to as a "vent tube," and is formed integrally with or otherwise coupled to the portion of shaft (204) extending proximally from balloon (206).

As shown best in FIG. 16, navigation sensor (250) is shown in the form of an annularly wound wire coil that encircles the distal end of catheter shaft (204) in a coaxial arrangement. Navigation sensor (250) is thus arranged externally of the distal vent tube portion of catheter shaft (204), and working lumen (234). Distal tip (212) encircles and encloses navigation sensor (250), such that navigation sensor (250) resides within an annular recess formed in an inner surface of distal tip (212). In the present example, wire (252) is arranged within working lumen (234) and includes a distal end that extends radially through shaft (204) to couple to annular navigation sensor (250). Wire (252) extends proximally through working lumen (234) and is arranged in communication with processor (606), for example via communication unit (614) described above.

As distal end (216) of balloon dilation catheter (200) is advanced through the electromagnetic field generated around the patient by field generators (602) of IGS navigation system (600), navigation sensor (250) generates electric signals that correspond to the location of navigation sensor (250) within the electromagnetic field. These signals are communicated proximally along wire (252) to processor (606). Processor (606) interprets these signals to determine the real-time location of navigation sensor (250), and thus of bulbous tip (212) of dilation catheter (200), within the electromagnetic field. As described above, processor (606) combines this information with the known internal anatomical layout of the patient to determine and communicate to the physician, via display screen (612), the real-time location of catheter distal end (216) within the patient. In this manner, the physician is able to monitor the precise location of catheter distal end (216) in real-time during a surgical procedure. This process facilitates accurate placement of dilation catheter (200) within the patient. For example, the physician may position catheter distal end (216) at a very specific location within the patient to thereby dilate a targeted portion of an anatomical passageway, such as ET (26), and/or to deliver a therapeutic substance from working lumen (234) through the open distal end (216). It will be appreciated that the image-guiding features of IGS navigation system (600) may be employed in combination with or in lieu of endoscope (400) described above.

C. Exemplary Internally Mounted Navigation Sensor

Figure 17:
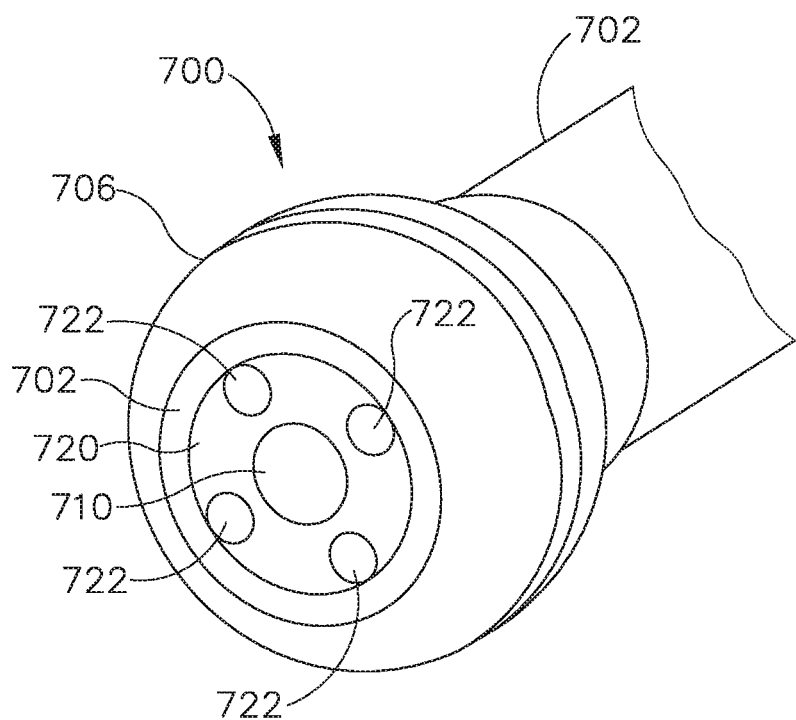
FIG. 17 depicts a perspective view of a distal end portion of another exemplary balloon dilation catheter.
Figure 18:
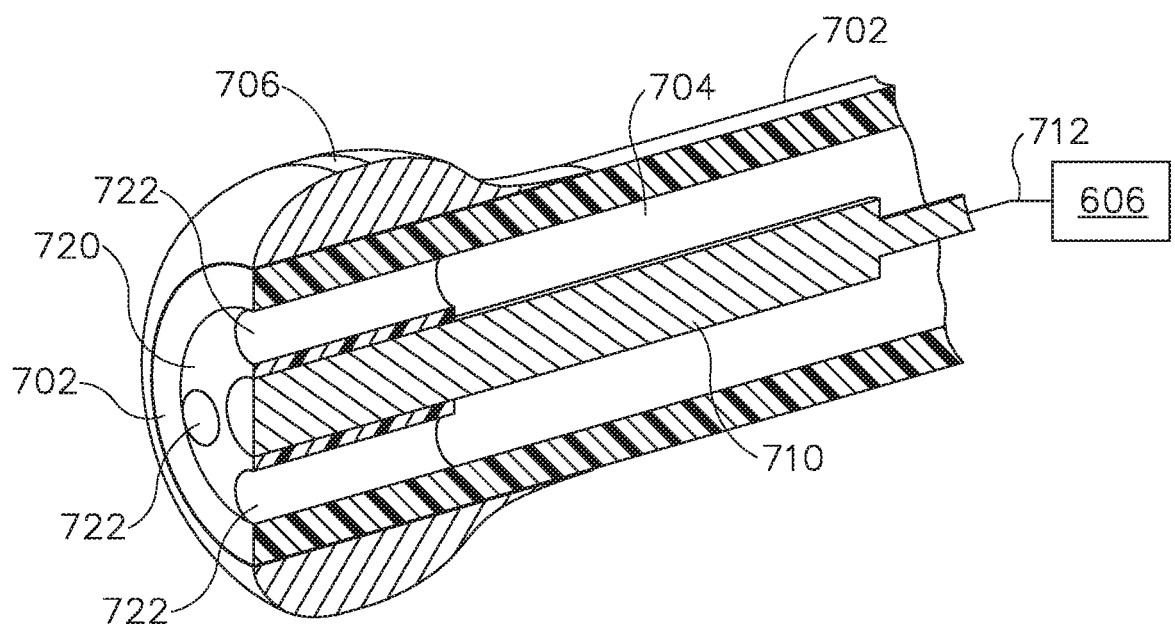
FIG. 18 depicts a side sectional view of the distal end portion of the balloon dilation catheter of FIG. 17.

FIGS. 17 and 18 show another exemplary balloon dilation catheter (700) configured for use with IGS navigation system (600). Dilation catheter (700) is similar to dilation catheter (200) described above except as otherwise described below. Dilation catheter (700) is similar to dilation catheter (200) in that dilation catheter (700) includes a proximal connector (not shown) similar to proximal connector (202), an elongate shaft (702) extending distally from the proximal connector and defining a working lumen (704), an expandable balloon (not shown) similar to balloon (206) arranged on a distal portion of shaft (702), and a bulbous tip (706) arranged at a distal end of shaft (702).

Dilation catheter (700) differs from dilation catheter (200) in that a navigation sensor (710) is supported coaxially within a distal end of working lumen (704) by a support structure (720). Navigation sensor (710) includes a cylindrical housing and a wire coil (not shown) arranged within the housing. Navigation sensor (710) is functionally similar to navigation sensor (250) described above. For instance, navigation sensor (710) is configured to generate electric signals corresponding to a location of navigation sensor (710) within an electromagnetic field generated about a portion of a patient, and is further configured to communicate those signals proximally along a wire (712) to processor (606).

Support structure (720) of balloon dilation catheter (700) is shown in the form of a cylindrical plug received within a distal end of shaft (702). Support plug (720) includes a plurality of vent passageways (722) spaced radially outwardly from and circumferentially about navigation sensor (710). Each vent passageway (722) extends axially through support plug (720) and opens to working lumen (704). Accordingly, each vent passageway (722) is configured to permit passage of air and, optionally, injection fluids therethrough, for example in a manner similar to that described above in connection with open distal end (216) of dilation catheter (200). While support plug (720) of the present example is shown having four passageways (722) of uniform size and circumferential spacing, it will be appreciated that various other quantities and configurations of vent passageways (722) may be provided in other examples.

D. Exemplary Internally Mounted Navigation Sensor with Hypotube Shield

Figure 19:
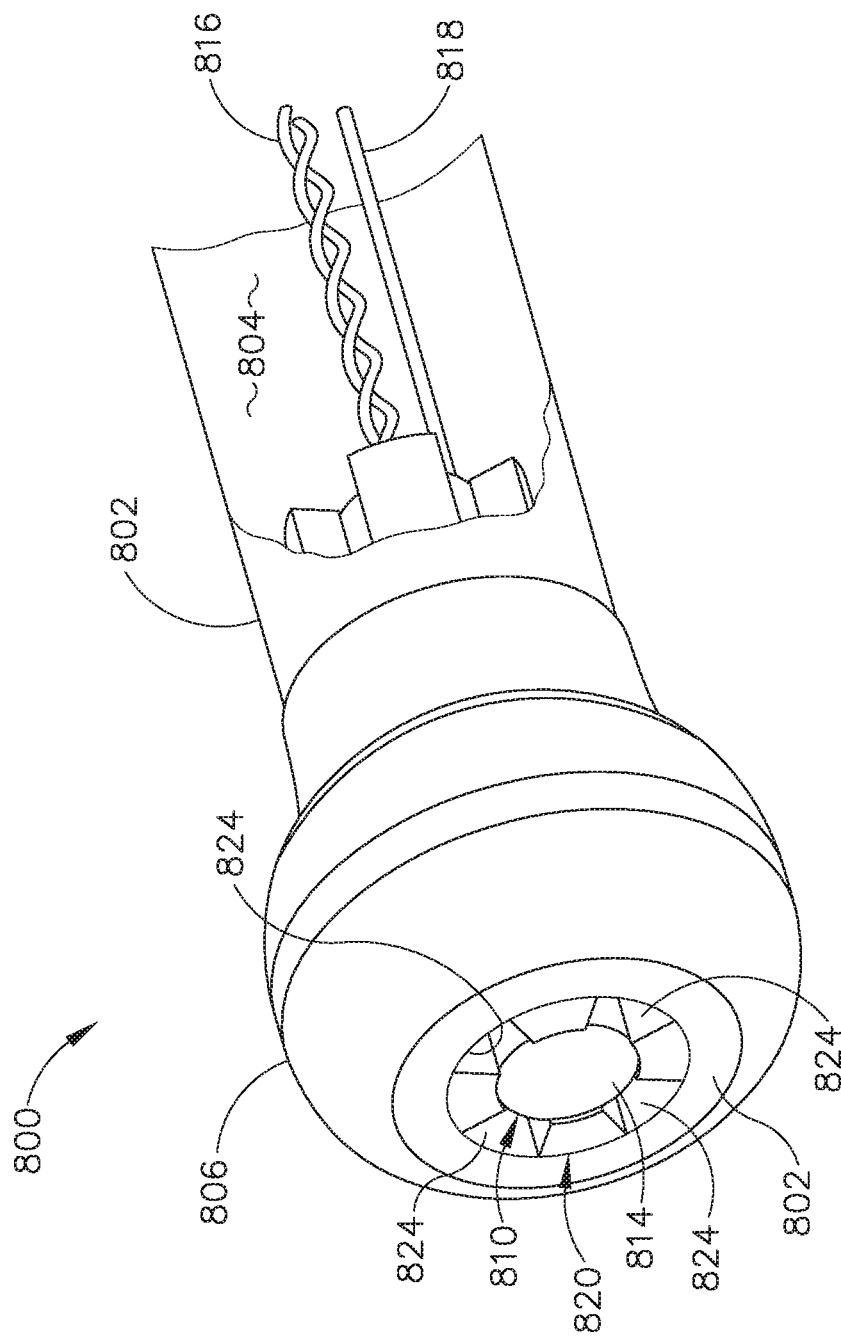
FIG. 19 depicts a perspective view of a distal end portion of another exemplary balloon dilation catheter.

FIG. 19 shows another exemplary balloon dilation catheter (800) configured for use with IGS navigation system (600). Dilation catheter (800) is similar to dilation catheters (200, 700) described above except as otherwise described below. Dilation catheter (800) is similar to dilation catheters (200, 700) in that dilation catheter (800) includes a proximal connector (not shown) similar to proximal connector (202), an elongate shaft (802) extending distally from the proximal connector and defining a working lumen (804), an expandable balloon (not shown) similar to balloon (206) arranged on a distal portion of shaft (802), and a bulbous tip (806) arranged at a distal end of shaft (802).

Figure 20:
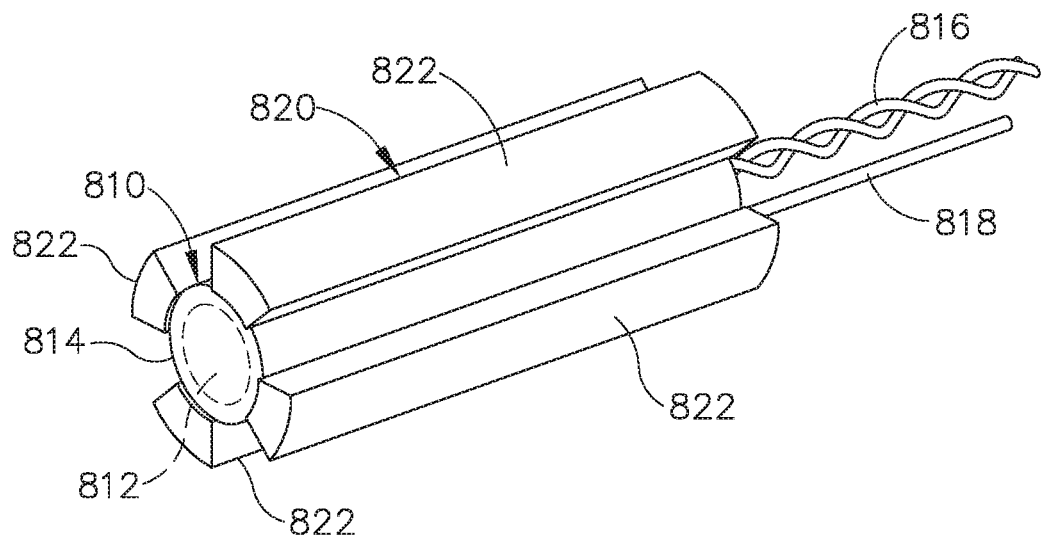
FIG. 20 depicts a distal end perspective view of a navigation sensor assembly of the balloon dilation catheter of FIG. 19.
Figure 21:
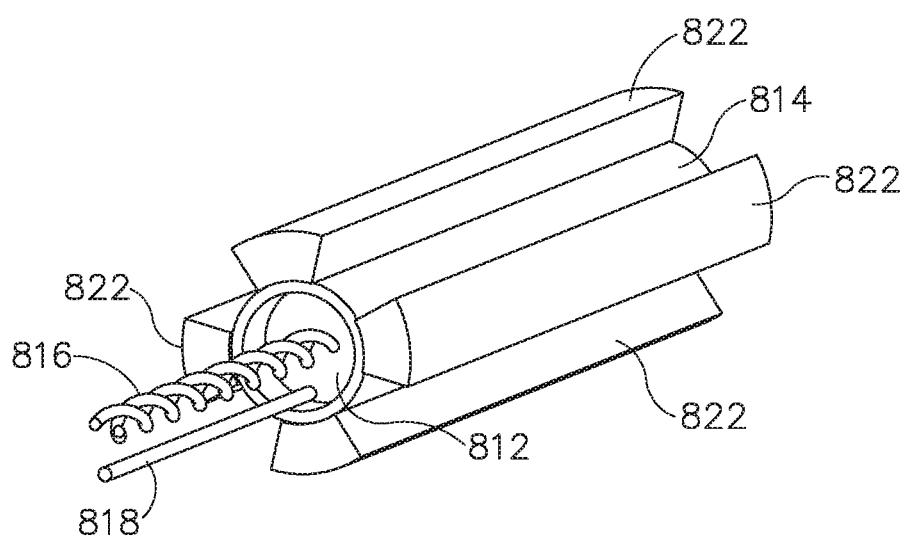
FIG. 21 depicts a proximal end perspective view of the navigation sensor assembly of FIG. 20.

Dilation catheter (800) further includes a navigation sensor assembly (810) supported coaxially within a distal end of working lumen (804) by a support structure (820). As shown best in FIGS. 20 and 21, navigation sensor assembly (810) includes a navigation sensor (812) similar to navigation sensor (710), and a hypotube shield (814) that encapsulates navigation sensor (812). Navigation sensor assembly (810) further includes a sensor wire (816) and a ground wire (818) each extending proximally through working lumen (804). Sensor wire (816) couples distally to navigation sensor (812) and proximally with processor (606), for example via communication unit (614), to communicate location signals generated by sensor (812) as sensor (812) moves through an electromagnetic field. Ground wire (818) is coupled distally to hypotube shield (814) and distally to an electrical ground. Though not shown, a similar ground wire may be provided in the other examples disclosed herein as well.

In the present example, support structure (820) comprises a plurality of axially extending support elements (822) spaced circumferentially about and coupled to hypotube shield (814). Support elements (822) are circumferentially spaced from one another to define a corresponding plurality of vent passageways (824) therebetween. Each vent passageway (824) is defined by an adjacent pair of support elements (822) and extends axially along hypotube shield (814) and an inner surface of shaft (802). Each vent passageway (824) opens proximally to working lumen (804)

and is configured to permit passage of air and, optionally, injection fluids therethrough, similar to vent passageways (722) of dilation catheter (700) and open distal end (216) of dilation catheter (200), for example. While support structure (820) of the present example is shown having four support elements (822) of uniform size and circumferential spacing, it will be appreciated that various other suitable quantities and configurations of support elements (822) or similar structures may be provided to define other quantities and configurations of vent passageways (824) in other examples.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation catheter comprising: (a) a catheter shaft having: (i) a proximal shaft portion defining a proximal shaft end, (ii) a distal shaft portion defining a distal shaft end, and (iii) a working lumen extending between the proximal and distal shaft ends; (b) an expandable element disposed on the distal shaft portion proximally of the distal shaft end, wherein the expandable element is configured to expand to dilate an anatomical passageway of a patient; and (c) a navigation sensor arranged at the distal shaft portion, distal to the expandable element, wherein the navigation sensor is configured to generate a signal corresponding to a location of the distal shaft portion within the patient.

Example 2

The dilation catheter of Example 1, wherein the navigation sensor comprises an electromagnetic sensor configured to generate an electric signal in response to movement of the electromagnetic sensor through an electromagnetic field.

Example 3

The dilation catheter of Example 2, wherein the electromagnetic sensor comprises a coil.

Example 4

The dilation catheter of any one or more of the preceding Examples, wherein the navigation sensor is arranged at the distal shaft end.

Example 5

The dilation catheter of any one or more of the preceding Examples, wherein the navigation sensor is arranged coaxially with the distal shaft portion.

Example 6

The dilation catheter of any one or more of the preceding Examples, wherein the navigation sensor is arranged externally of the catheter shaft.

Example 7

The dilation catheter of any one or more of the preceding Examples, further comprising a distal tip disposed at the distal shaft end, wherein the navigation sensor is arranged within the distal tip.

Example 8

The dilation catheter of Example 7, wherein the distal tip includes at least one vent passageway that opens to the working lumen.

Example 9

The dilation catheter of any one or more of Examples 1 through 5, wherein the navigation sensor is arranged within the working lumen at the distal shaft end.

Example 10

The dilation catheter of any one or more of the preceding Examples, wherein the navigation sensor is housed within a hypotube shield.

Example 11

The dilation catheter of Example 9, further comprising a support structure arranged within the working lumen at the distal shaft end, wherein the support structure is configured to support the navigation sensor within the working lumen.

Example 12

The dilation catheter of Example 11, wherein the support structure comprises a plug.

Example 13

The dilation catheter of Example 11, wherein the support structure comprises a plurality of support elements arranged circumferentially about the navigation sensor.

Example 14

The dilation catheter of any one or more of Examples 11 through 13, wherein the support structure defines at least one vent passageway that opens to the working lumen

Example 15

The dilation catheter of any one or more of the preceding Examples, further comprising a bulbous distal tip arranged at the distal shaft end, wherein the bulbous distal tip has a maximum outer diameter that is greater than a maximum outer diameter of at least the proximal shaft portion of the catheter shaft.

Example 16

The dilation catheter of any one or more of the preceding Examples, wherein the catheter shaft further includes an inflation lumen spaced radially from the working lumen, wherein the inflation lumen communicates with an interior of the expandable element.

Example 17

A dilation catheter comprising: (a) a catheter shaft having: (i) a proximal shaft end, (ii) a distal shaft end, and (iii) a working lumen extending between the proximal and distal shaft ends; (b) an expandable element disposed on the catheter shaft, wherein the expandable element is configured to expand to dilate an anatomical passageway of a patient; (c) a bulbous tip arranged at the distal shaft end; and (d) a navigation sensor arranged within the bulbous tip, wherein the navigation sensor is configured to generate a signal corresponding to a location of the bulbous tip within the patient.

Example 18

The dilation catheter of Example 17, wherein the navigation sensor comprises an electromagnetic sensor, wherein the electromagnetic sensor is configured to generate an electric signal in response to movement of the electromagnetic sensor through an electromagnetic field.

Example 19

A system for dilating an anatomical passageway of a patient, the system comprising: (a) a guide member, wherein the guide member includes a guide member shaft having a guide lumen and a distal opening configured to provide access to the anatomical passageway; and (b) a dilation catheter, wherein the dilation catheter is slidably received within the guide lumen, wherein the dilation catheter comprises: (i) a catheter shaft having: (A) a proximal shaft end, (B) a distal shaft end, and (C) a working lumen extending between the proximal and distal shaft ends, (ii) an expandable element disposed on the catheter shaft, wherein the expandable element is configured to expand to dilate the anatomical passageway, and (iii) a navigation sensor, wherein the navigation sensor is configured to generate a signal corresponding to a location of the navigation sensor within the patient, wherein the navigation sensor is positioned distally in relation to the expandable element.

Example 20

The system of Example 19, wherein the navigation sensor comprises an electromagnetic sensor arranged at a distal portion of the dilation catheter, wherein the electromagnetic sensor is configured to generate an electric signal in response to movement of the electromagnetic sensor through an electromagnetic field, wherein the electric signal corresponds to a location of the distal portion within the patient.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user/physician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, examples, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A dilation catheter comprising:
   (a) a catheter shaft having:
      (i) a proximal shaft portion defining a proximal shaft end,
      (ii) a distal shaft portion defining a distal shaft end, and
      (iii) a working lumen extending between the proximal and distal shaft ends;
   (b) an expandable element disposed on the distal shaft portion proximally of the distal shaft end, wherein the expandable element is configured to expand to dilate an anatomical passageway of a patient;
   (c) a navigation sensor arranged at the distal shaft portion externally of the working lumen, distal to the expandable element, wherein the navigation sensor is configured to generate a signal corresponding to a location of the distal shaft portion within the patient; and
   (d) a distal tip disposed at the distal shaft end, wherein the navigation sensor is arranged within the distal tip.

2. The dilation catheter of claim 1, wherein the navigation sensor comprises an electromagnetic sensor configured to generate an electric signal in response to movement of the electromagnetic sensor through an electromagnetic field.

3. The dilation catheter of claim 2, wherein the electromagnetic sensor comprises a coil.

4. The dilation catheter of claim 3, wherein the coil extends circumferentially about an exterior surface of the distal shaft end of the catheter shaft.

5. The dilation catheter of claim 2, further comprising at least one field generating element configured to generate the electromagnetic field around a portion of the patient containing an anatomical passageway through which the catheter shaft is inserted.

6. The dilation catheter of claim 2, further comprising a processor, wherein the processor is configured to receive the electric signal and determine a location of the distal shaft portion within the patient based on the electric signal.

7. The dilation catheter of claim 6, further comprising a wire, wherein the wire is configured to electrically couple the navigation sensor to the processor, wherein the wire is positioned within the working lumen.

8. The dilation catheter of claim 1, wherein the navigation sensor is arranged coaxially with the distal shaft portion.

9. The dilation catheter of claim 1, wherein the navigation sensor is arranged externally of the catheter shaft.

10. The dilation catheter of claim 1, wherein the distal tip includes at least one vent passageway that opens to the working lumen.

11. The dilation catheter of claim 1, wherein the distal tip includes a bulbous distal tip arranged at the distal shaft end, wherein the bulbous distal tip has a maximum outer diameter that is greater than a maximum outer diameter of at least the proximal shaft portion of the catheter shaft.

12. The dilation catheter of claim 11, further comprising an annular recess formed in an inner surface of the bulbous distal tip, wherein the navigation sensor resides within the annular recess.

13. The dilation catheter of claim 1, wherein the catheter shaft further includes an inflation lumen spaced radially from the working lumen, wherein the inflation lumen communicates with an interior of the expandable element.

14. A dilation catheter comprising:
   (a) a catheter shaft having:
      (i) a proximal shaft end,
      (ii) a distal shaft end, and
      (iii) a working lumen extending between the proximal and distal shaft ends;
   (b) an expandable element disposed on the catheter shaft, wherein the expandable element is configured to expand to dilate an anatomical passageway of a patient;
   (c) a bulbous tip arranged at the distal shaft end; and
   (d) a navigation sensor arranged within the bulbous tip on an exterior surface of the catheter shaft, wherein the navigation sensor is configured to generate a signal corresponding to a location of the bulbous tip within the patient.

15. The dilation catheter of claim 14, wherein the navigation sensor comprises an electromagnetic sensor, wherein the electromagnetic sensor is configured to generate an electric signal in response to movement of the electromagnetic sensor through an electromagnetic field.

16. The dilation catheter of claim 15, wherein the electromagnetic sensor comprises a coil.

17. The dilation catheter of claim 16, wherein the coil extends circumferentially about an exterior surface of the catheter shaft.

18. The dilation catheter of claim 14, wherein the navigation sensor is arranged coaxially with the distal shaft end.

19. The dilation catheter of claim 14, wherein the catheter shaft further includes an inflation lumen spaced radially from the working lumen, wherein the inflation lumen communicates with an interior of the expandable element.

20. A dilation catheter comprising:
   (a) a catheter shaft having:
      (i) a proximal shaft end,
      (ii) a distal shaft end, and
      (iii) a working lumen extending between the proximal and distal shaft ends;
   (b) an expandable element disposed on the distal shaft end, wherein the expandable element is configured to expand to dilate an anatomical passageway of a patient;
   (c) a distal tip disposed at the distal shaft end, wherein the distal tip is configured to surround a portion of the distal shaft end; and
   (d) a navigation sensor arranged within the distal tip, wherein the navigation sensor is positioned exterior to the distal shaft end, wherein the navigation sensor is configured to generate a signal corresponding to a location of the distal shaft end within the patient.

* * * * *